(12) United States Patent
Inokuchi et al.

(10) Patent No.: US 9,090,932 B2
(45) Date of Patent: Jul. 28, 2015

(54) METHOD FOR SCREENING OF THERAPEUTIC AGENT FOR HYPERLIPEMIA

(75) Inventors: Jinichi Inokuchi, Miyagi (JP); Masakazu Nagafuku, Miyagi (JP); Hirotaka Hayamizu, Niigata (JP)

(73) Assignee: Japan Science and Technology Agency, Saitama (JP)

( * ) Notice: Subject to any disclaimer, the term of this patent is extended or adjusted under 35 U.S.C. 154(b) by 0 days.

(21) Appl. No.: 13/511,028

(22) PCT Filed: Nov. 25, 2010

(86) PCT No.: PCT/JP2010/070959
§ 371 (c)(1),
(2), (4) Date: May 21, 2012

(87) PCT Pub. No.: WO2011/065389
PCT Pub. Date: Jun. 3, 2011

(65) Prior Publication Data
US 2012/0244539 A1    Sep. 27, 2012

(30) Foreign Application Priority Data
Nov. 27, 2009    (JP) .................................. 2009-269593

(51) Int. Cl.
| C12Q 1/00 | (2006.01) |
| C12Q 1/48 | (2006.01) |
| C12Q 1/60 | (2006.01) |
| C12Q 1/61 | (2006.01) |
| A61K 45/06 | (2006.01) |

(52) U.S. Cl.
CPC . *C12Q 1/48* (2013.01); *A61K 45/06* (2013.01); *C12Q 1/60* (2013.01); *C12Q 1/61* (2013.01); *G01N 2333/91148* (2013.01); *G01N 2405/10* (2013.01); *G01N 2500/02* (2013.01); *G01N 2800/044* (2013.01); *G01N 2800/324* (2013.01)

(58) Field of Classification Search
USPC ............................................................ 435/4
See application file for complete search history.

(56) References Cited

U.S. PATENT DOCUMENTS

2007/0224200 A1*  9/2007  Elbawab et al. ........... 424/146.1

FOREIGN PATENT DOCUMENTS

| EP | 1 726 313 A1 | 11/2006 |
| JP | 2003-238410 A | 8/2003 |
| JP | 2003238410 A * | 8/2003 |
| WO | WO 02/084301 A2 | 10/2002 |

OTHER PUBLICATIONS

Holland et al., Lipid mediators of insulin resistance. Nutrition Reviews, vol. 65 No. 6 (Jun. 2007) S39-S46.*
Ishii et al., Expressing cloning and functional characterization of human cDNA for ganglioside GM3 synthase. Journal of Biological Chemistry, vol. 273 (Nov. 27, 1998) pp. 31652-31655.*
Bilj et al., Reduction of glycosphingolipid biosynthesis stimulates biliary lipid secretion in mice. Hepatology, vol. 49 (Feb. 2009) pp. 637-645.*
Langeveld et al., Glycosphingolipids and insulin resistance. Progress in Lipid Research, vol. 48 No. 3-4 (May-Jul. 2009) pp. 196-205.*
Hasty et al., Severe hypercholesterolemia, hypertriglyceridemia and atherosclerosis in mice lacking both leptin and the low density lipoprotein receptor. The Journal of Biological Chemistry, vol. 276 No. 40 (Oct. 5, 2001) pp. 37402-37408.*
Aerts et al., "Pharmacological Inhibition of Glucosylceramide Synthase Enhances Insulin Sensitivity,". Diabetes, May 2007, 56:1341-1349/.
Bijl et al., "Reduction of Glycosphingolipid Biosynthesis Stimulates Biliary Lipid Secretion in Mice," Hepatology, Feb. 2009, 49:637-645.
Inokuchi et al., "Preparation of the active isomer of 1-phenyl-2-decanoylamino-3-morpholino-1-propanol, inhibitor of murine glucocerebroside synthetase," Journal of Lipid Research, 1987, 28:565-571.
Tagami et al., "Ganglioside GM3 Participates in the Pathological Conditions of Insulin Resistance," The Journal of Biological Chemistry, Feb. 1, 2002, 277(5):3085-3092.
Van Eijk et al., "Reducing Glycosphingolipid Content in Adipose Tissue of Obese Mice Restores Insulin Sensitivity, Adipogenesis and Reduces Inflammation," PLoS One, epub Mar. 2009, 4(3):e4723, 11 pages.
Yamashita et al., "A vital role for glycosphingolipid synthesis during development and differentiation," Proc. Natl. Acad. Sci., USA, Aug. 1999, 96:9142-9147.
Yamashita et al., "Enhanced insulin sensitivity in mice lacking ganglioside GM3," PNAS, Mar. 18, 2003, 100(6):3445-3449.
Zhao et al., "Inhibiting Glycosphingolipid Synthesis Improves Glycemic Control and Insulin Sensitivity in Animal Models of Type 2 Diabetes," Diabetes, May 2007, 56:1210-1218.
Zhao et al., "Inhibiting Glycosphingolipid Synthesis Ameliorates Hepatic Steatosis in Obese Mice," Hepatology, 2009, 50:85-93.

* cited by examiner

*Primary Examiner* — Jon P Weber
*Assistant Examiner* — Kara Johnson
(74) *Attorney, Agent, or Firm* — Foley & Lardner LLP

(57) ABSTRACT

Disclosed are a highly safe treatment method for hyperlipidemia and a therapeutic agent for hyperlipidemia. Specifically, the invention provides a novel method for screening an agent for treating hyperlipidemia, more specifically, a method for screening a substance that can inhibit the production or function of gangliosides, particularly GM3, or inhibit the activity or expression of GM3 synthase to reduce a blood lipid level. A pharmaceutical composition, which can specifically inhibit the production of gangliosides, particularly GM3, thereby effective for hyperlipidemia treatment, and others are also provided.

4 Claims, 10 Drawing Sheets

SEQUENCE LISTING

```
<160> NUMBER OF SEQ ID NOS: 8

<210> SEQ ID NO 1
<211> LENGTH: 1188
<212> TYPE: DNA
<213> ORGANISM: Homo sapiens
<220> FEATURE:
<221> NAME/KEY: misc_feature
<222> LOCATION: (1)..(1188)
<223> OTHER INFORMATION: Human SAT-I
<220> FEATURE:
<221> NAME/KEY: CDS
<222> LOCATION: (1)..(1188)

<400> SEQUENCE: 1 atg gct tct gtt cca atg cca agt gag tac acc tat gtg aaa ctg aga        48
Met Ala Ser Val Pro Met Pro Ser Glu Tyr Thr Tyr Val Lys Leu Arg
1               5                   10                  15 agt gat tgc tcg agg cct tcc ctg caa tgg tac acc cga gct caa agc        96
Ser Asp Cys Ser Arg Pro Ser Leu Gln Trp Tyr Thr Arg Ala Gln Ser
                20                  25                  30 aag atg aga agg ccc agc ttg tta tta aaa gac atc ctc aaa tgt aca       144
Lys Met Arg Arg Pro Ser Leu Leu Leu Lys Asp Ile Leu Lys Cys Thr
            35                  40                  45 ttg ctt gtg ttt gga gtg tgg atc ctt tat atc ctc aag tta aat tat       192
Leu Leu Val Phe Gly Val Trp Ile Leu Tyr Ile Leu Lys Leu Asn Tyr
        50                  55                  60 act act gaa gaa tgt gac atg aaa aaa atg cat tat gtg gac cct gac       240
Thr Thr Glu Glu Cys Asp Met Lys Lys Met His Tyr Val Asp Pro Asp
65                  70                  75                  80 cat gta aag aga gct cag aaa tat gct cag caa gtc ttg cag aag gaa       288
His Val Lys Arg Ala Gln Lys Tyr Ala Gln Gln Val Leu Gln Lys Glu
                85                  90                  95 tgt cgt ccc aag ttt gcc aag aca tca atg gcg ctg tta ttt gag cac       336
Cys Arg Pro Lys Phe Ala Lys Thr Ser Met Ala Leu Leu Phe Glu His
                100                 105                 110
```

| | | |
|---|---|---|
| agg tat agc gtg gac tta ctc cct ttt gtg cag aag gcc ccc aaa gac<br>Arg Tyr Ser Val Asp Leu Leu Pro Phe Val Gln Lys Ala Pro Lys Asp<br>115                            120                        125 | | 384 |
| agt gaa gct gag tcc aag tac gat cct cct ttt ggg ttc cgg aag ttc<br>Ser Glu Ala Glu Ser Lys Tyr Asp Pro Pro Phe Gly Phe Arg Lys Phe<br>130                          135                      140 | | 432 |
| tcc agt aaa gtc cag acc ctc ttg gaa ctc ttg cca gag cac gac ctc<br>Ser Ser Lys Val Gln Thr Leu Leu Glu Leu Leu Pro Glu His Asp Leu<br>145                          150                      155                      160 | | 480 |
| cct gaa cac ttg aaa gcc aag acc tgt cgg cgc tgt gtg gtt att gga<br>Pro Glu His Leu Lys Ala Lys Thr Cys Arg Arg Cys Val Val Ile Gly<br>                  165                      170                      175 | | 528 |
| agc gga gga ata ctg cac gga tta gaa ctg ggc cac acc ctg aac cag<br>Ser Gly Gly Ile Leu His Gly Leu Glu Leu Gly His Thr Leu Asn Gln<br>              180                      185                      190 | | 576 |
| ttc gat gtt gtg ata agg tta aac agt gca cca gtt gag gga tat tca<br>Phe Asp Val Val Ile Arg Leu Asn Ser Ala Pro Val Glu Gly Tyr Ser<br>                  195                      200                      205 | | 624 |
| gaa cat gtt gga aat aaa act act ata agg atg act tat cca gag ggc<br>Glu His Val Gly Asn Lys Thr Thr Ile Arg Met Thr Tyr Pro Glu Gly<br>210                          215                      220 | | 672 |
| gca cca ctg tct gac ctt gaa tat tat tcc aat gac tta ttt gtt gct<br>Ala Pro Leu Ser Asp Leu Glu Tyr Tyr Ser Asn Asp Leu Phe Val Ala<br>225                          230                      235                      240 | | 720 |
| gtt tta ttt aag agt gtt gat ttc aac tgg ctt caa gca atg gta aaa<br>Val Leu Phe Lys Ser Val Asp Phe Asn Trp Leu Gln Ala Met Val Lys<br>                  245                      250                      255 | | 768 |
| aag gaa acc ctg cca ttc tgg gta cga ctc ttc ttt tgg aag cag gtg<br>Lys Glu Thr Leu Pro Phe Trp Val Arg Leu Phe Phe Trp Lys Gln Val<br>                        260                      265                      270 | | 816 |
| gca gaa aaa atc cca ctg cag cca aaa cat ttc agg att ttg aat cca<br>Ala Glu Lys Ile Pro Leu Gln Pro Lys His Phe Arg Ile Leu Asn Pro<br>                  275                      280                      285 | | 864 |
| gtt atc atc aaa gag act gcc ttt gac atc ctt cag tac tca gag cct<br>Val Ile Ile Lys Glu Thr Ala Phe Asp Ile Leu Gln Tyr Ser Glu Pro<br>290                          295                      300 | | 912 |
| cag tca agg ttc tgg ggc cga gat aag aac gtc ccc aca atc ggt gtc<br>Gln Ser Arg Phe Trp Gly Arg Asp Lys Asn Val Pro Thr Ile Gly Val<br>305                          310                      315                      320 | | 960 |
| att gcc gtt gtc tta gcc aca cat ctg tgc gat gaa gtc agt ttg gcg<br>Ile Ala Val Val Leu Ala Thr His Leu Cys Asp Glu Val Ser Leu Ala<br>                  325                      330                      335 | | 1008 |
| ggt ttt gga tat gac ctc aat caa ccc aga aca cct ttg cac tac ttc<br>Gly Phe Gly Tyr Asp Leu Asn Gln Pro Arg Thr Pro Leu His Tyr Phe<br>                  340                      345                      350 | | 1056 |
| gac agt caa tgc atg gct gct atg aac ttt cag acc atg cat aat gtg<br>Asp Ser Gln Cys Met Ala Ala Met Asn Phe Gln Thr Met His Asn Val<br>                  355                      360                      365 | | 1104 |
| aca acg gaa acc aag ttc ctc tta aag ctg gtc aaa gag gga gtg gtg<br>Thr Thr Glu Thr Lys Phe Leu Leu Lys Leu Val Lys Glu Gly Val Val<br>370                          375                      380 | | 1152 |
| aaa gat ctc agt gga ggc att gat cgt gaa ttt tga<br>Lys Asp Leu Ser Gly Gly Ile Asp Arg Glu Phe<br>385                          390                      395 | | 1188 |

```
<210> SEQ ID NO 2
<211> LENGTH: 395
<212> TYPE: PRT
<213> ORGANISM: Homo sapiens

<400> SEQUENCE: 2
```

Met Ala Ser Val Pro Met Pro Ser Glu Tyr Thr Tyr Val Lys Leu Arg
1               5                   10                  15

Ser Asp Cys Ser Arg Pro Ser Leu Gln Trp Tyr Thr Arg Ala Gln Ser
            20                  25                  30

Lys Met Arg Arg Pro Ser Leu Leu Leu Lys Asp Ile Leu Lys Cys Thr
        35                  40                  45

Leu Leu Val Phe Gly Val Trp Ile Leu Tyr Ile Leu Lys Leu Asn Tyr
50                  55                  60

Thr Thr Glu Glu Cys Asp Met Lys Lys Met His Tyr Val Asp Pro Asp
65              70                  75                  80

His Val Lys Arg Ala Gln Lys Tyr Ala Gln Gln Val Leu Gln Lys Glu
                85                  90                  95

Cys Arg Pro Lys Phe Ala Lys Thr Ser Met Ala Leu Leu Phe Glu His
            100                 105                 110

Arg Tyr Ser Val Asp Leu Leu Pro Phe Val Gln Lys Ala Pro Lys Asp
        115                 120                 125

Ser Glu Ala Glu Ser Lys Tyr Asp Pro Pro Phe Gly Phe Arg Lys Phe
130                 135                 140

Ser Ser Lys Val Gln Thr Leu Leu Glu Leu Leu Pro Glu His Asp Leu
145                 150                 155                 160

Pro Glu His Leu Lys Ala Lys Thr Cys Arg Arg Cys Val Val Ile Gly
                165                 170                 175

Ser Gly Gly Ile Leu His Gly Leu Glu Leu Gly His Thr Leu Asn Gln
            180                 185                 190

Phe Asp Val Val Ile Arg Leu Asn Ser Ala Pro Val Glu Gly Tyr Ser
        195                 200                 205

Glu His Val Gly Asn Lys Thr Thr Ile Arg Met Thr Tyr Pro Glu Gly
210                 215                 220

Ala Pro Leu Ser Asp Leu Glu Tyr Tyr Ser Asn Asp Leu Phe Val Ala
225                 230                 235                 240

Val Leu Phe Lys Ser Val Asp Phe Asn Trp Leu Gln Ala Met Val Lys
                245                 250                 255

Lys Glu Thr Leu Pro Phe Trp Val Arg Leu Phe Phe Trp Lys Gln Val
            260                 265                 270

Ala Glu Lys Ile Pro Leu Gln Pro Lys His Phe Arg Ile Leu Asn Pro
        275                 280                 285

Val Ile Ile Lys Glu Thr Ala Phe Asp Ile Leu Gln Tyr Ser Glu Pro
290                 295                 300

Gln Ser Arg Phe Trp Gly Arg Asp Lys Asn Val Pro Thr Ile Gly Val
305                 310                 315                 320

Ile Ala Val Val Leu Ala Thr His Leu Cys Asp Glu Val Ser Leu Ala
                325                 330                 335

Gly Phe Gly Tyr Asp Leu Asn Gln Pro Arg Thr Pro Leu His Tyr Phe
            340                 345                 350

Asp Ser Gln Cys Met Ala Ala Met Asn Phe Gln Thr Met His Asn Val
        355                 360                 365

Thr Thr Glu Thr Lys Phe Leu Leu Lys Leu Val Lys Glu Gly Val Val
370                 375                 380

Lys Asp Leu Ser Gly Gly Ile Asp Arg Glu Phe
385                 390                 395

<210> SEQ ID NO 3
<211> LENGTH: 1245

```
<212> TYPE: DNA
<213> ORGANISM: Mus musculus
<220> FEATURE:
<221> NAME/KEY: misc_feature
<222> LOCATION: (1)..(1245)
<223> OTHER INFORMATION: Mouse SAT-I
<220> FEATURE:
<221> NAME/KEY: CDS
<222> LOCATION: (1)..(1245)

<400> SEQUENCE: 3 atg cac aca gag gcg gtg ggc ggc gcg gcg cgg agg ccc cag aag ctg      48
Met His Thr Glu Ala Val Gly Gly Ala Ala Arg Arg Pro Gln Lys Leu
1               5                   10                  15 cga agc caa gca gcg gca cct gcc tgc cga gca atg cca agt gag ttc      96
Arg Ser Gln Ala Ala Ala Pro Ala Cys Arg Ala Met Pro Ser Glu Phe
            20                  25                  30 acc tct gca aag ctg aga agt gat tgc tca agg acc tcc ctg caa tgg     144
Thr Ser Ala Lys Leu Arg Ser Asp Cys Ser Arg Thr Ser Leu Gln Trp
        35                  40                  45 tac acc cga acc cag cac aag atg aga aga ccc agc ttg tta ata aaa     192
Tyr Thr Arg Thr Gln His Lys Met Arg Arg Pro Ser Leu Leu Ile Lys
    50                  55                  60 gac atc tgc aag tgc acg ttg gtt gca ttt gga gtc tgg ctc ctg tac     240
Asp Ile Cys Lys Cys Thr Leu Val Ala Phe Gly Val Trp Leu Leu Tyr
65                  70                  75                  80 atc ctc att ttg aat tac acc gct gaa gaa tgt gac atg aaa aga atg     288
Ile Leu Ile Leu Asn Tyr Thr Ala Glu Glu Cys Asp Met Lys Arg Met
                85                  90                  95 cac tat gtg gac cct gac cgg ata aag aga gct cag agc tat gct cag     336
His Tyr Val Asp Pro Asp Arg Ile Lys Arg Ala Gln Ser Tyr Ala Gln
            100                 105                 110 gaa gtc ttg cag aag gaa tgt cgg ccc agg tac gcg aag acg gct atg     384
Glu Val Leu Gln Lys Glu Cys Arg Pro Arg Tyr Ala Lys Thr Ala Met
        115                 120                 125 gct ctg tta ttt gag gac agg tac agc atc aac ttg gag cct ttt gtg     432
Ala Leu Leu Phe Glu Asp Arg Tyr Ser Ile Asn Leu Glu Pro Phe Val
    130                 135                 140 cag aag gtc ccc acg gcc agt gaa gct gag ctc aag tat gac ccg cct     480
Gln Lys Val Pro Thr Ala Ser Glu Ala Glu Leu Lys Tyr Asp Pro Pro
145                 150                 155                 160 ttt gga ttc cgg aag ttc tcc agt aaa gtc cag agc ctc ttg gat atg     528
Phe Gly Phe Arg Lys Phe Ser Ser Lys Val Gln Ser Leu Leu Asp Met
                165                 170                 175 ctg ccc gaa cat gac ttt cct gaa cac ttg aga gcc aag gcc tgc aag     576
Leu Pro Glu His Asp Phe Pro Glu His Leu Arg Ala Lys Ala Cys Lys
            180                 185                 190 cgc tgt gtg gtt gtt ggg aac ggg ggc atc ctg cac gga cta gag ctg     624
Arg Cys Val Val Val Gly Asn Gly Gly Ile Leu His Gly Leu Glu Leu
        195                 200                 205 ggt cac gcc ctc aac cag ttc gat gtg gta ata agg ttg aac agt gcg     672
Gly His Ala Leu Asn Gln Phe Asp Val Val Ile Arg Leu Asn Ser Ala
    210                 215                 220 cca gtt gag ggt tac tct gaa cac gtt ggg aat aaa act act ata agg     720
Pro Val Glu Gly Tyr Ser Glu His Val Gly Asn Lys Thr Thr Ile Arg
225                 230                 235                 240 atg act tac cca gag ggt gcg cca ctg tcg gac gtt gaa tac tac gcc     768
Met Thr Tyr Pro Glu Gly Ala Pro Leu Ser Asp Val Glu Tyr Tyr Ala
                245                 250                 255 aat gat ttg ttc gtt act gtt tta ttt aag agt gtt gat ttc aag tgg     816
Asn Asp Leu Phe Val Thr Val Leu Phe Lys Ser Val Asp Phe Lys Trp
            260                 265                 270
```

```
ctt caa gca atg gta aaa aat gaa agc ctg ccc ttt tgg gtt cgc ctc      864
Leu Gln Ala Met Val Lys Asn Glu Ser Leu Pro Phe Trp Val Arg Leu
        275                 280                 285 ttc ttt tgg aag caa gtg gca gaa aaa gtc cca ctc cag cca aag cac      912
Phe Phe Trp Lys Gln Val Ala Glu Lys Val Pro Leu Gln Pro Lys His
290                 295                 300 ttc agg att ttg aac cca gtt atc atc aaa gaa act gcc ttc gac atc      960
Phe Arg Ile Leu Asn Pro Val Ile Ile Lys Glu Thr Ala Phe Asp Ile
305                 310                 315                 320 ctt cag tac tca gag cct cag tca aga ttc tgg ggc cat gat aag aac     1008
Leu Gln Tyr Ser Glu Pro Gln Ser Arg Phe Trp Gly His Asp Lys Asn
            325                 330                 335 atc ccc acg atc ggc gtc att gcc gtt gtc ttg gct aca cat ctg tgt     1056
Ile Pro Thr Ile Gly Val Ile Ala Val Val Leu Ala Thr His Leu Cys
            340                 345                 350 gat gaa gtc agc ctg gca ggc ttt ggc tac gac ctc agt caa ccc agg     1104
Asp Glu Val Ser Leu Ala Gly Phe Gly Tyr Asp Leu Ser Gln Pro Arg
            355                 360                 365 acc cct ctg cac tac ttt gac agt cag tgc atg ggc gcc atg cac tgg     1152
Thr Pro Leu His Tyr Phe Asp Ser Gln Cys Met Gly Ala Met His Trp
370                 375                 380 cag gtc atg cac aat gtg acc aca gag acc aag ttc ctc ctg aag ctc     1200
Gln Val Met His Asn Val Thr Thr Glu Thr Lys Phe Leu Leu Lys Leu
385                 390                 395                 400 ctc aag gag ggc gtg gtg gag gac ctc agc ggc ggc atc cac tga        1245
Leu Lys Glu Gly Val Val Glu Asp Leu Ser Gly Gly Ile His
            405                 410
```

<210> SEQ ID NO 4
<211> LENGTH: 414
<212> TYPE: PRT
<213> ORGANISM: Mus musculus

<400> SEQUENCE: 4

```
Met His Thr Glu Ala Val Gly Gly Ala Ala Arg Arg Pro Gln Lys Leu
1               5                   10                  15

Arg Ser Gln Ala Ala Ala Pro Ala Cys Arg Ala Met Pro Ser Glu Phe
            20                  25                  30

Thr Ser Ala Lys Leu Arg Ser Asp Cys Ser Arg Thr Ser Leu Gln Trp
        35                  40                  45

Tyr Thr Arg Thr Gln His Lys Met Arg Arg Pro Ser Leu Leu Ile Lys
    50                  55                  60

Asp Ile Cys Lys Cys Thr Leu Val Ala Phe Gly Val Trp Leu Leu Tyr
65                  70                  75                  80

Ile Leu Ile Leu Asn Tyr Thr Ala Glu Glu Cys Asp Met Lys Arg Met
                85                  90                  95

His Tyr Val Asp Pro Asp Arg Ile Lys Arg Ala Gln Ser Tyr Ala Gln
            100                 105                 110

Glu Val Leu Gln Lys Glu Cys Arg Pro Arg Tyr Ala Lys Thr Ala Met
        115                 120                 125

Ala Leu Leu Phe Glu Asp Arg Tyr Ser Ile Asn Leu Glu Pro Phe Val
    130                 135                 140

Gln Lys Val Pro Thr Ala Ser Glu Ala Glu Leu Lys Tyr Asp Pro Pro
145                 150                 155                 160

Phe Gly Phe Arg Lys Phe Ser Ser Lys Val Gln Ser Leu Leu Asp Met
                165                 170                 175

Leu Pro Glu His Asp Phe Pro Glu His Leu Arg Ala Lys Ala Cys Lys
```

```
                180             185             190
    Arg Cys Val Val Gly Asn Gly Gly Ile Leu His Gly Leu Glu Leu
                195             200             205
    Gly His Ala Leu Asn Gln Phe Asp Val Val Ile Arg Leu Asn Ser Ala
                210             215             220
    Pro Val Glu Gly Tyr Ser Glu His Val Gly Asn Lys Thr Thr Ile Arg
    225             230             235             240
    Met Thr Tyr Pro Glu Gly Ala Pro Leu Ser Asp Val Glu Tyr Tyr Ala
                245             250             255
    Asn Asp Leu Phe Val Thr Val Leu Phe Lys Ser Val Asp Phe Lys Trp
                260             265             270
    Leu Gln Ala Met Val Lys Asn Glu Ser Leu Pro Phe Trp Val Arg Leu
                275             280             285
    Phe Phe Trp Lys Gln Val Ala Glu Lys Val Pro Leu Gln Pro Lys His
                290             295             300
    Phe Arg Ile Leu Asn Pro Val Ile Ile Lys Glu Thr Ala Phe Asp Ile
    305             310             315             320
    Leu Gln Tyr Ser Glu Pro Gln Ser Arg Phe Trp Gly His Asp Lys Asn
                325             330             335
    Ile Pro Thr Ile Gly Val Ile Ala Val Val Leu Ala Thr His Leu Cys
                340             345             350
    Asp Glu Val Ser Leu Ala Gly Phe Gly Tyr Asp Leu Ser Gln Pro Arg
                355             360             365
    Thr Pro Leu His Tyr Phe Asp Ser Gln Cys Met Gly Ala Met His Trp
                370             375             380
    Gln Val Met His Asn Val Thr Thr Glu Thr Lys Phe Leu Leu Lys Leu
    385             390             395             400
    Leu Lys Glu Gly Val Val Glu Asp Leu Ser Gly Gly Ile His
                405             410
```

```
<210> SEQ ID NO 5
<211> LENGTH: 25
<212> TYPE: DNA
<213> ORGANISM: Artificial Sequence
<220> FEATURE:
<223> OTHER INFORMATION: Primer

<400> SEQUENCE: 5
ggaatccatc cctttctca cagag                                        25

<210> SEQ ID NO 6
<211> LENGTH: 22
<212> TYPE: DNA
<213> ORGANISM: Artificial Sequence
<220> FEATURE:
<223> OTHER INFORMATION: Primer

<400> SEQUENCE: 6
tgaactcact tggcattgct gg                                          22

<210> SEQ ID NO 7
<211> LENGTH: 25
<212> TYPE: DNA
<213> ORGANISM: Artificial Sequence
<220> FEATURE:
<223> OTHER INFORMATION: Primer

<400> SEQUENCE: 7
ggaatccatc cctttctca cagag                                        25
```

```
<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
tgaactcact tggcattgct gg                                              22
```

METHOD FOR SCREENING OF THERAPEUTIC AGENT FOR HYPERLIPEMIA

CROSS-REFERENCE TO RELATED APPLICATIONS

This application is a National Stage application of PCT/JP2010/070959, filed Nov. 25, 2010, which claims priority from Japanese application JP 2009-269593, filed Nov. 27, 2009.

The instant application contains a Sequence Listing which has been submitted in ASCII format via EFS-WEB and is hereby incorporated by reference in its entirety. Said ASCII copy, created on May 18, 2012, is named sequence.txt and is 20 KB.

TECHNICAL FIELD

The present invention provides a method for screening a novel therapeutic agent for hyperlipidemia. More specifically, the present invention provides a method for screening a substance that provides a blood lipid level lowering activity through inhibiting the production or function of gangliosides, particularly GM3, or inhibiting the activity or expression of GM3 synthase. The present invention also provides a pharmaceutical composition effective for treating hyperlipidemia that specifically inhibits the synthesis of gangliosides, particularly GM3, and others.

BACKGROUND ART

Circulatory disorders associated with arteriosclerosis including myocardial infarction, cerebral infarction, etc. are increasing yearly and are one of the leading causes of death in adults. There are various causes to induce arteriosclerosis and hyperlipidemia (including hypercholesteremia, hypertriglyceridemia, etc.) is recognized to be one of the most important causes. For the purpose of treating hypercholesteremia, drugs such as HMG-CoA reductase inhibitors (especially, statin type medicaments), anionic exchange resin drugs, etc. have been used. However, these drugs not only inhibit cholesterol biosynthesis but also inhibit the biosynthesis of some other components such as ubiquinone, dolichol and heme A, which are essential for the living body. It is thus concerned that adverse effects caused thereby might take place.

In recent years, the importance of glycosphingolipids (GSLs) in various metabolic disorders (including insulin resistance, type 2 diabetes mellitus, hyperlipidemia, arteriosclerosis, fatty liver, etc.) caused by obesity has been revealed. GSL falls in a molecular group formed by the addition of various sugar chains to the backbone of ceramide and is present in blood or on cell membranes of all cells. GSL is biosynthesized in vivo through a series of enzyme reactions starting from ceramide (FIG. 1). GSL containing sialic acid is called a ganglioside family and starts from GM3 which is synthesized from lactocylceramide (LacCer) by GM3 synthase (sialic acid transferase I: SAT-I) (FIG. 1). Inhibitors to the enzymes involved in biosynthesis of glucosylceramide (GlcCer), which is the early stage of GSL biosynthesis pathway, include: D-threo-1-phenyl-2-decanoylamino-3-morpholino-1-propanol (D-threo-PDMP) (Non-Patent Document 1), (1R,2R)-nonanoic acid [2-(2,3-dihydro-benzo[1,4]dioxin-6-yl)-2-hydroxy-1-pyrrolidin-1-ylmethyl-ethyl]-amide-1-tartaric acid salt (Genz-123346), which is a D-threo-PDMP analog, N-(5-adamantane-1-yl-methoxy)-pentyl-1-deoxynojirimycin (AMP-DNM), etc. These inhibitors are reported improving insulin resistance in vitro and in obese animal models, having an effect of improving fatty liver and even promoting excretion of free fatty acids (and reducing cholesterol to promote excretion of cholesterol from the liver into the bile (i.e., activation of the reverse cholesterol transport system), etc. (Non-Patent Documents 2 to 7). Thus, development toward clinical applications is ongoing.

However, it is reported that glucosylceramide synthase knockout mice caused embryonic lethality (Non-Patent Document 8) and hence, there is also a concern of potential adverse effects of inhibitors of this enzyme. On the other hand, the life span of GM3 synthase knockout mice is equivalent to that of wild-type mice (Non-Patent Document 9). It is therefore expected that adverse effects caused by inhibition of GM3 synthase may be minimized.

GSLs found in insulin-responsible organs (such as muscle, liver and adipose tissue) are highly diverse and include glucosylceramides (GlcCer), lactosylceramides (LacCer) and gangliosides GM3 and GM2. Yamashita et al. established GM3 synthase (SAT-I) knockout mice and reported that gangliosides of the a- and b-series, which are normally expressed as shown in FIG. 1, were not expressed in the mice, and when the onset of high-fat diet-induced insulin resistance was compared with the onset in the wild-type mice, insulin resistance was reduced in the SAT-I knockout mice (Non-Patent Document 9).

[Non-Patent Document 1] Inokuchi J. & Radin N. (1987) J. Lipid Res. 28, 565-571

[Non-Patent Document 2] Tagami S., Inokuchi J., Kabayama K., Yoshimura H., Kitamura F., Uemura S., Ogawa C., Ishii A., Saito M., Ohtsuka Y., et al. (2002) J. Biol. Chem. 277, 3085-3092

[Non-Patent Document 3] Zhao H., Przybylska M., Wu I. H., Zhang J., Siegel C., Komarnitsky S., Yew N. S., & Cheng S. H. (2007) Diabetes 56, 1210-1218

[Non-Patent Document 4] Zhao H., Przybylska M., Wu I. H., Zhang J., Maniatis P., Pacheco J., Piepenhagen P., Copeland D., Arbeeny C., Shayman J. A., et al. (2009) Hepatology 50, 85-93

[Non-Patent Document 5] Aerts J. M., Ottenhoff R., Powlson A. S., Grefhorst A., van Eijk M., Dubbelhuis P. F., Aten J., Kuipers F., Serlie M. J., Wennekes T., et al. (2007) Diabetes 56, 1341-1349

[Non-Patent Document 6] van Eijk M., Aten J., Bijl N., Ottenhoff R., van Roomen C. P., Dubbelhuis P. F., Seeman I., Ghauharali-van der Vlugt K., Overkleeft H. S., Arbeeny C., et al. (2009) PLoS One 4, e4723. Epub. 2009 March 4723

[Non-Patent Document 7] Bijl N., van Roomen C. P., Triantis V., Sokolovic M., Ottenhoff R., Scheij S., van Eijk M., Boot R. G, Aerts J. M., & Groen A. K. (2009) Hepatology 49, 637-645

[Non-Patent Document 8] YAMASHTA, T., et al, Proc. Natl. Acad. Sci. USA, Vol. 96, pp. 9142-9147, 1999

[Non-Patent Document 9] Yamashita T., Hashiramoto A., Haluzik M., Mizukami H., Beck S., Norton A., Kono M., Tsuji S., Daniotti J. L., Werth N., et al. (2003) Proc. Natl. Acad. Sci. USA 100, 3445-3449

DISCLOSURE OF THE INVENTION

Technical Problem

Therefore, the present inventors have examined lipid metabolism abnormality, as a target disease for treatment based on GM3 synthase regulation, in order to provide a means which provides a novel and highly safe drug for treating hyperlipidemia and a method for preventing/treating hyperlipidemia.

Solution of Problem

The present inventors made extensive efforts to solve the problem described above, prepared the double knockout mice (SAT-I/apoE KO mice) where the gene involved in ganglioside biosynthesis (GM3 synthase gene) and the gene for apolipoprotein E (apoE) were knocked out, and analyzed, on an individual level, the functional role of gangliosides in various obesity-caused metabolic disorders. As a result, it has been found that a blood lipid level (including a blood cholesterol level and/or a blood triglyceride level) could be reduced through inhibiting GM3 synthase. The present invention has thus been accomplished.

Accordingly, the present invention provides a method for screening a substance that reduces a blood lipid level (including a blood cholesterol level and/or a blood triglyceride level), which is effective for treating hyperlipidemia, a pharmaceutical composition effective for treating hyperlipidemia which selectively inhibits synthesis of gangliosides (particularly GM3), and others.

Specifically, the present invention relates to the screening method, pharmaceutical composition, treatment method, etc., described below.

[1] A method for screening a substance having a blood lipid level lowering activity, which comprises:
 (i) administering a test substance to a non-human animal, and,
 (ii) determining the blood lipid level in the non-human animal.

[2] A method for screening a substance having a blood lipid level lowering activity, which comprises:
 (i) contacting GM3 synthase with a substrate thereof in the presence or absence of a test substance,
 (ii) selecting a test substance that decreases the synthesized amount of GM3,
 (iii) administering the selected test substance to a non-human animal, and,
 (iv) determining the blood lipid level in the non-human animal.

[3] A method for screening a substance having blood lipid level lowering activity, which comprises:
 (i) contacting a test substance with a cell expressing GM3 synthase,
 (ii) selecting a test substance that decreases the expression level of GM3 synthase,
 (iii) administering the selected test substance to a non-human animal, and,
 (iv) determining the blood lipid level in the non-human animal.

[4] The method according to [3] above, wherein the cell expressing GM3 synthase is selected from the group consisting of adipocytes, hepatocytes, vascular endothelial cells, vascular smooth muscle cells, epithelial cells, neurocytes, fibroblasts, monocytes and macrophages.

[5] The method according to [3] above, wherein the cell expressing GM3 synthase is a transformant produced by genetic engineering.

[6] The screening method according to any one of [1] to [5] above, which further comprises screening a test substance that reduces a blood cholesterol level and/or a blood triglyceride level.

[7] The method according to any one of [1] to [6] above, wherein the non-human animal has a higher blood lipid level than normal level.

[8] The method according to any one of [1] to [7] above, wherein the non-human animal is a mouse.

[9] A pharmaceutical composition effective for treatment of hyperlipidemia, comprising a substance that specifically prevents a production of a ganglioside.

[9a] A pharmaceutical composition effective for treatment of hyperlipidemia, comprising a substance that selectively suppresses a function of a ganglioside.

[10] The composition according to [9], wherein the ganglioside is GM3.

[11] A pharmaceutical composition effective for treatment of hyperlipidemia, comprising an antibody against GM3, a GM3 synthase inhibitor or a substance that inhibits GM3 synthase expression.

[12] A method for treating hyperlipidemia which comprises administering an effective dose of a pharmaceutical composition effective for treatment of hyperlipidemia to a non-human animal to reduce a blood lipid level.

[13] The method according to [12], wherein the pharmaceutical composition reduces a blood cholesterol level and/or a blood triglyceride level.

[14] The method according to [12] or [13], wherein the pharmaceutical composition comprises a substance that selectively inhibits production of a ganglioside.

[15] The method according to [14], wherein the ganglioside is GM3.

[16] The method according to [15], wherein the substance that selectively inhibits the ganglioside production is an antibody against GM3, a GM3 synthase inhibitor or a substance that inhibits GM3 synthase expression.

[17] A method for regulating a blood lipid level with an antibody against GM3 or a GM3 synthase inhibitor, or by inhibiting GM3 synthase expression.

Advantageous Effect of Invention

The pharmaceutical composition of the present invention inhibits ganglioside GM3 biosynthesis to reduce a blood lipid level (including a blood cholesterol level and/or a blood triglyceride level), and can provide a new method for treating hyperlipidemia even from a clinical viewpoint.

BRIEF DESCRIPTION OF DRAWINGS

FIG. 2A shows the targeting vector (top), a wild-type gene (second row), and a variant gene (third row).

FIG. 2B shows determination of the SAT-I genotype by PCR. Ex2 marked with the arrow designates normal SAT-I gene exon 2, and Neo marked with the arrow designates the neomycin resistant gene.

FIG. 2C shows the results of TLC analysis of brain gangliosides.

FIG. 3A shows the breeding scheme for generating SAT-I/apoE double knockout mice.

FIG. 3B is a Western Blot showing expression of apoE. The band at the position marked with the arrow shows apoE protein, lane C1 designates normal mouse and lane C2 designates a control sample for the apoE single knockout mouse.

FIG. 3C shows a PCR gel. Lane C3 designates the control sample for the SAT-I single knockout mouse. Ex2 marked with the arrow designates normal SAT-I gene exon 2, and Neo marked with the arrow designates the neomycin resistant gene.

FIG. 4A shows the body weight for each strain.

FIG. 4B shows the total cholesterol level for each strain.

FIG. 4C shows plasma triglyceride levels for each strain.

FIG. 4D shows the free fatty acid levels for each strain.

EMBODIMENTS FOR CARRYING OUT THE INVENTION

1. Screening Method of the Invention

Figure 1:
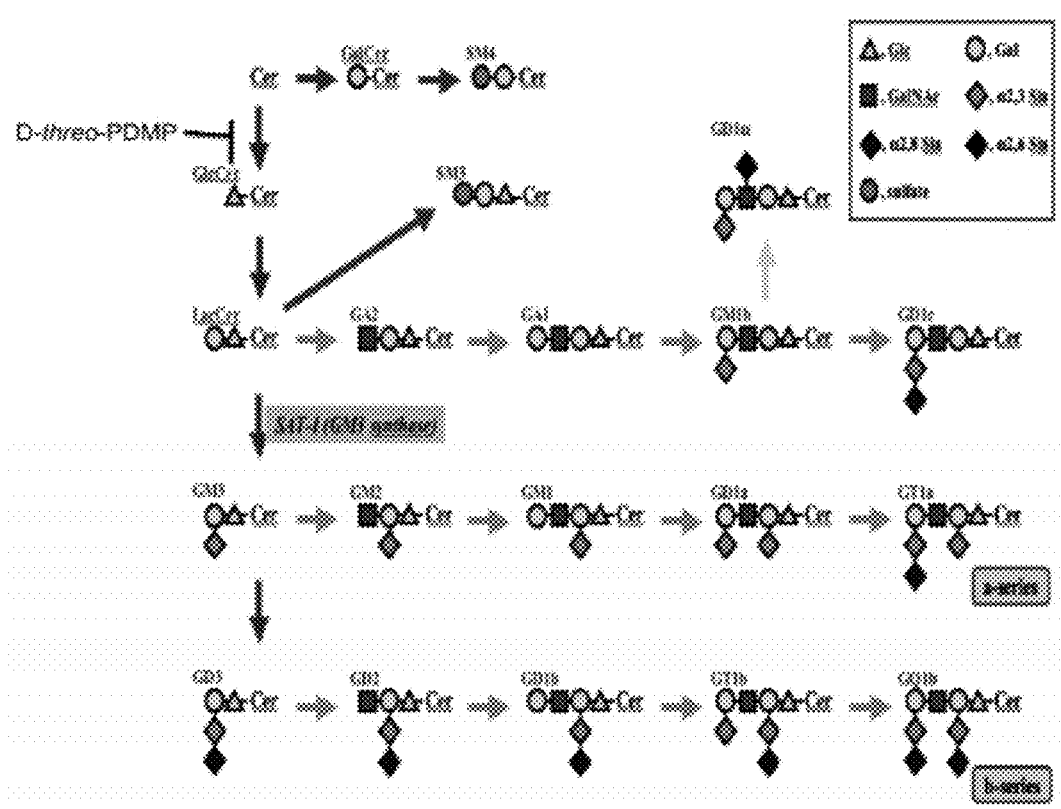
FIG. 1 shows the ganglioside biosynthesis pathway.

The present invention provides a method for screening a substance having a blood lipid level lowering activity, namely, an activity of reducing a blood cholesterol level and/or blood triglyceride level, which comprises: (i) administering a test substance to a non-human animal, and (ii) determining the blood lipid level in the non-human animal. Examples of the test substance include a peptide, a protein, a nonpeptidic compound, a synthetic compound, a fermentation product, a cell extraction liquid, a plant extraction liquid, an animal tissue extraction liquid, plasma, etc. The test substance administered may be used solely or in multiple combination manner. In determining the blood lipid level, there may be used known methods as in the aforesaid assay methods, etc.

As used herein, the term "substance having a blood lipid level lowering activity" is intended to mean a substance that reduces a cholesterol level and/or a triglyceride level in blood. Specifically, the "substance having a blood lipid level lowering activity", as used herein, refers to a substance that has the cholesterol level and/or the triglyceride level lowering activities in a sample (plasma) obtained from the subject, who received the substance, by 10% or more, preferably 20% or more, more preferably 40% or more, much more preferably 60% or more, and most preferably 80% or more, as compared to the control, when assayed according to the method described in KISO SEIKAGAKU JIKKENHO (Basic Biochemical Experiments), Vol. 5, Shishitsu, Toshitsu, Fukugotoshitsu (Lipids, Carbohydrates and Glycoconjugates) (edited by The Japanese Biochemical Society). In this case, the reduction is limited to nearly normal blood lipid level.

The blood lipid level in a sample from the subject can be determined through known methods utilizing the enzyme method, the immunodiffusion method or the like. Such methods include, for example, the methods described in KISO SEIKAGAKU JIKKENHO (Basic Biochemical Experiments), Vol. 5, Shishitsu, Toshitsu, Fukugotoshitsu (Lipids, Carbohydrates and Glycoconjugates) (edited by The Japanese Biochemical Society) described above. In addition, assay kits for triglycerides and cholesterol are also commercially available from various manufacturers. Examples are Cholesterol E-Test Wako (Wako Pure Chemical Industries, Ltd) for the cholesterol assay kit, TG-EN Kainos (Kainos Laboratories) for the triglyceride assay kit, and NEFA C-Test Wako (Wako Pure Chemical Industries, Ltd) for the free fatty acid assay kit.

The screening method of the present invention may be any of the methods developed to date as the methods for assaying cholesterol and triglycerides. In more detail, the screening method of the present invention may further include the step with high performance liquid chromatography (HPLC) or gas chromatography. Regarding detailed principles or the like, see, e.g., KISO SEIKAGAKU JIKKENHO (Basic Biochemical Experiments), Vol. 5, Shishitsu, Toshitsu, Fukugotoshitsu (Lipids, Carbohydrates and Glycoconjugates) (edited by The Japanese Biochemical Society).

As used herein, the term "reduces a blood cholesterol level and/or a blood triglyceride level" is intended to mean to reduce the cholesterol level and/or the triglyceride level in blood by 10% or more, preferably 20% or more, more preferably 40% or more, much more preferably 60% or more, and most preferably 80% or more, in terms of the concentration of at least one of the cholesterol and triglyceride, as compared to the control, when assayed through the conventional method described above. However, the reduction is limited to nearly normal blood lipid level.

The substance that reduces a blood lipid level (including a blood cholesterol level and/or a blood triglyceride level) is effective for treating or preventing hyperlipidemia. As used herein, the term "hyperlipidemia" is also called hyperlipoproteinemia and refers to such a condition that a plasma lipid other than free fatty acids is elevated. Healthy adults have, in plasma, 150 to 220 mg/dl of cholesterols, 50 to 140 mg/dl of triacylglycerols and 150 to 220 mg/dl of phospholipids, and they are bound to apolipoproteins and dispersed as lipoproteins. Hyperlipidemia may be classified into hyperlipidemia where triacylglycerols are mainly increased (e.g., type I hyperlipidemia, type IV hyperlipidemia and type V hyperlipidemia), and hyperlipidemia where cholesterol is mainly increased (e.g., familial hypercholesteremia, familial complicated hyperlipidemia and type III hyperlipidemia) (Mariko Shiba, et al., SHIN SEIKAGAKU JIKKEN KOZA (New Series of Biochemical Experiments), Vol. 4, "Shishitsu I: Chusei Shishitsu-to-III Gata Koshiketsusho (Lipid I: Neutral Lipids and Lipoproteins)," published by Tokyo Kagaku Dojin Publishing Co., 1993, Chapter 11).

The substance that reduces the blood lipid level is not only effective for treating or preventing hyperlipidemia but also effective for treating or preventing at least one disease selected from arteriosclerosis, atherosclerosis, peripheral vascular disease, hyper LDLemia, hypo HDLemia, hypercholesteremia, hypertriglyceridemia, familial hypercholesteremia, cardiovascular disturbance, angina pectoris, ischemia, cardiac ischemia, thrombosis, myocardial infarction, reperfusion damage, angioplasty restenosis and hypertension.

Examples of the non-human animal as the subject used in the screening method described above include animals which are generally utilized in tests of pharmaceutical products, such as a monkey, chimpanzee, dog, cat, guinea pig, rat, mouse, rabbit, pig, sheep, horse, etc., preferably, a monkey, chimpanzee, rabbit, rat and mouse, and more preferably, a mouse or rat.

In the present invention, the substance having the blood lipid level lowering activity may be a substance that can specifically inhibit the function of GM3, or may be substance that can selectively inhibit a specific function in various functions of GM3. The glycosphingolipid as used herein refers to a lipid comprising a saccharide, a fatty acid and a sphingosine which is a long-chain base in the molecule. The ganglioside as used herein collectively refers to the family of sphingoglycolipids containing sialic acid, and is a molecule in which a sugar chain containing sialic acid is covalently bound to a lipid called ceramide. Today, gangliosides with various sugar chain structures are known, and GM3 is the first ganglioside molecule in the biosynthesis pathway (see FIG. 1). That is, all endogenous ganglio-type gangliosides are biosynthesized through a series of enzyme reactions in which ceramide is used as a starting material and a GM3 synthase triggers the first step. During the series of reactions, GM3 is a molecule that is the origin of all gangliosides, and is synthesized from lactosylceramide by GM3 synthase (SAT-I). The sugar chain moiety is sequentially synthesized by glycosyltransferase in the lumen of the Golgi body in the cell using a sugar nucleotide as a donor.

In a specific biosynthesis pathway of ganglio-type gangliosides, GM3 is produced from Gal-Glc-Cer by GM3 synthase (SAT-I), and then, from this GM3, various gangliosides including the a-series (GM3, GM2, GM1, GD1a and GT1a), the b-series (GD3, GD2, GD1b, GT1b and GQ1b) and the c-series (GT3, GT2, GT1c, GQ1c and GP1c) are produced, as shown in FIG. 1. It is understood from the figure that production of these ganglioside molecules is dependent on GM3 synthase. In view of this, GM3 has the functions as the starting material for other gangliosides.

It is also reported that GM3 plays the functions of various growth factor receptors (Inokuchi J. and Kabayama K. (2007) Receptor Modifications in Glycobiology. Comprehensive Glycoscience 3, 733-744. (Elsevier Science & Technology)) or the functions to regulate molecular transporters (Glaros EN., et al. Glycosphingolipid Accumulation Inhibits Cholesterol Efflux via the ABCA1/Apolipoprotein A-I Pathway J. Biol. Chem. 280, 24515-24523, 2005). Furthermore, with regard to GM3 functions, a new molecular mechanism has recently been proposed on unresponsiveness to insulin signaling where GM3 serves to dissociate insulin receptors from caveolae (Kabayama K., et al., Glycobiology (2005) 15, 21-29, Kabayama K., et al., Proc. Natl. Acad. Sci. USA (2007) 104, 13678-13683).

In the present invention, the substance having the blood lipid level lowering activity may be an antibody against GM3, which specifically or selectively inhibits a function of GM3. Such an antibody includes a known monoclonal antibody specific to GM3 (Kotani, M., et al., Biochem. Biophys. Acta, 1117, 97-103 (1992)). In one specific embodiment, the antibody may inhibit a function of GM3 on cell membranes of cells including primary culture cells obtained from adipocytes, hepatocytes, vascular endothelial cells, vascular smooth muscle cells, epithelial cells, fibroblasts, monocytes, macrophages, etc., and various cell lines (e.g., mouse 3T3-L1 in adipocytes; human HepG2 in hepatocytes; in endothelial cells, immortalized endothelial cell lines having an acetylated LDL uptake activity; RAW264.7 in macrophages; etc., but not limited to these cell lines). In the context of the present application, it is understood that the antibody includes a monoclonal antibody, a polyclonal antibody, an anti-idiotype antibody, an antibody fragment (e.g., Fab, F(ab')$_2$, Fv variable region or complementarity-determining region). It is understood that, when the antibody is bound with Ka of $10^{-7}$ M or more, preferably $10^{-8}$ M or more, the antibody is specific to an antigen, namely, GM3 or GM3 synthase. The affinity of the monoclonal antibody can be easily determined by those skilled in the art (see Scatchard, Ann. N.Y. Acad. Sci. 51: 660-672, 1949).

In the present invention, the substance having the blood lipid level lowering activity may be "a GM3 synthase inhibitor," namely, a substance that specifically inhibits the GM3 biosynthesis. As used herein, the GM3 synthase (SAT-I) refers to a protein comprising the amino acid sequence of SEQ ID NO: 2 or 4, or the amino acid sequence of SEQ ID NO: 2 or 4 having mutations of deletion, substitution, insertion and/or addition of one to several (1 to 9, 1 to 8, 1 to 7, 1 to 6, 1 to 5, 1 to 4, 1 to 3, 1 to 2, or 1) amino acid(s) therein. In the biosynthesis of GM3, glucosylceramide synthase acts on ceramide (Cer) to synthesize glucosylceramide (GlcCer), and then lactosylceramide (LacCer) is produced by lactosylceramide synthase, as shown in FIG. 1. The GM3 synthase recognizes this LacCer as a substrate to synthesize GM3. That is, examples include those which can reduce the amount of GM3 synthesized via competitive inhibition of enzyme reactions with substrate analogs of glucosylceramide synthase, lactosylceramide synthase and GM3 synthase, or non-competitively through binding to these enzymes.

In the present invention, the substance having the blood lipid level lowering activity may be "a substance that specifically inhibits GM3 synthase expression." As used herein, cDNA of GM3 synthase (SAT-I) is represented by, for example, SEQ ID NO: 1 or 3. Examples of the substance that specifically inhibits GM3 synthase expression include an antisense nucleic acid, a ribozyme and a dsRNA having RNAi effect, etc.

As used herein, the term "nucleic acid" is interchangeably used with "polynucleotide", "gene" or "nucleic acid molecule", and is intended to mean a polymer of nucleotide. As used herein, the term "base sequence" is interchangeably used with "nucleic acid sequence" or "nucleotide sequence", and is represented as a sequence of deoxyribonucleotide (abbreviated as A, G, C and T). Furthermore, the "polynucleotide comprising the base sequence of SEQ ID NO: 1 or a fragment thereof" is intended to mean a polynucleotide comprising a sequence represented by the respective deoxynucleotides A, G, C and/or T of SEQ ID NO: 1 or a fragment thereof.

The nucleic acid in accordance with the present invention may be present in the form of RNA (e.g., mRNA) or DNA (e.g., cDNA or genomic DNA). DNA may be a double strand or a single strand. A single-stranded DNA or RNA may be a coding strand (also known as "sense strand") or a noncoding strand (also known as "antisense strand").

As used herein, the "substance that inhibits the expression of GM3 synthase" includes suppression of transcription of the GM3 synthase gene and suppression of translation into a protein. Moreover, it also includes complete stop of DNA expression as well as reduction of DNA expression.

One embodiment of the "substance that inhibits GM3 synthase expression" is a nucleic acid encoding the antisense chain complementary to the GM3 synthase gene. The antisense technology is publicly known as a method for specifically suppressing the expression of a particular endogenous gene, and is described in various documents (for example, see Hirashima and Inoue, "Shin Seikagaku Jikken Koza 2, Kakusan IV, Idenshi No Fukusei To Hatsugen (New Biochemistry Experimentation Lectures 2, Nucleic Acids IV, Replication and Expression of Gene)", edited by Japanese Biochemistry Society, Tokyo Kagaku Dojin Co., Ltd., pp. 319-347, 1993;

etc.). The antisense nucleic acid can be prepared, for example, based on information of the sequence of cDNA represented by SEQ ID NO: 1 or 3 according to the phosphorothionate method (Stein, Nucleic Acids Res., 16: 3209-3221, 1988) or others. The nucleic acid prepared can be utilized in the form directly applied to a cell according to a publicly-known method. Also, the nucleic acid can transform a desired cell in the form that the nucleic acid is incorporated into a vector having a known expression system and appropriately expressed. Preferably, the sequence of the antisense nucleic acid is complementary to the transcription product of an endogenous gene possessed by a cell to be transformed, while the sequence does not have to be completely complementary thereto as long as gene expression can be effectively inhibited. Preferably, the transcribed RNA has at least 90% (e.g., at least 95%, at least 96%, at least 97%, at least 98%, and at least 99%) complementarity to the transcription product of a target gene. For effectively inhibiting expression of the target gene using the antisense sequence, the length of the antisense nucleic acid is at least 15 bases, preferably at least 100 bases, and more preferably at least 500 bases. Usually, the length of the antisense nucleic acid to be used is less than 5 kb, and preferably less than 2.5 kb.

In the present invention, the expression of an endogenous GM3 synthase gene can also be suppressed by utilizing DNA encoding a ribozyme. The ribozyme is intended to mean an RNA molecule having a catalytic activity, and cleaves the transcription product of a target DNA to inhibit the function of the gene. Regarding the design of ribozymes, reference can be made to various known documents (see, e.g., FEBS Lett. 228: 228, 1988; FEBS Lett. 239: 285, 1988; Nucl. Acids Res. 17: 7059, 1989; Nature 323: 349, 1986; Nucl. Acids Res. 19: 6751, 1991; Protein Eng 3: 733, 1990; Nucl. Acids Res. 19: 3875, 1991; Nucl. Acids Res. 19: 5125, 1991; Biochem. Biophys. Res. Commun. 186: 1271, 1992, etc.). Furthermore, the "polynucleotide encoding an RNA which suppresses DNA expression through a co-suppression effect" refers to a nucleotide which inhibits the function of a target DNA by 'co-suppression.'"

Moreover, the suppression of an endogenous gene expression in the present invention can also be achieved by transforming a desired cell with a gene having a dominant negative character of a target gene. The gene having a dominant negative character is intended to mean a gene having the function to extinguish or reduce the activity of an endogenous wild-type gene inherent to a desired cell, by expressing the gene.

Another embodiment of the nucleic acid to be used for suppressing the expression of GM3 synthase gene is RNA that suppresses DNA expression by RNAi effect. The term "RNAi" is intended to mean a phenomenon in which, when a double-stranded RNA having a sequence that is identical with or similar to a target gene sequence is introduced into a cell, expression of both the exogenous gene introduced and the target endogenous gene is suppressed. As used herein, RNA includes, for example, double-stranded RNA having 21 to 25 nucleotides causing RNA interference, such as dsRNA (double strand RNA), siRNA (small interfering RNA) and shRNA (short hairpin RNA). Such RNA may also be locally delivered to a desired site by the delivery system of liposomes or the like, and may be locally expressed using a vector in which the above-described double-strand RNA can be produced. Methods for preparing and using such a double-stranded RNA (dsRNA, siRNA or shRNA) are publicly known from many documents (see, e.g., Japanese Laid-Open Patent Application Publication (Translation of PCT Application) No. 2002-516062; USPA No. 2002/086356A; Nature Genetics, 24(2), 180-183, 2000 February; Genesis, 26(4), 240-244, 2000 April; Nature, 407:6802, 319-20, 2002 Sep. 21; Genes & Dev., Vol. 16(8), 948-958, 2002 Apr. 15; Proc. Natl. Acad. Sci. USA., 99(8), 5515-5520, 2002 Apr. 16; Science, 296(5567), 550-553, 2002 Apr. 19; Proc Natl. Acad. Sci. USA, 99:9, 6047-6052, 2002 Apr. 30; Nature Biotechnology, Vol. 20 (5), 497-500, 2002 May; Nature Biotechnology, Vol. 20(5), 500-505, 2002 May; Nucleic Acids Res., 30:10, e46, 2002 May 15, etc.).

The screening method of the present invention may further include performing primary screening for a test substance in vitro before the test substance is administered to a non-human animal. In more detail, the method may include the steps of contacting glycosphingolipid synthase with a substrate thereof in the presence or absence of a test substance and selecting a test substance which reduces the amount of the product synthesized. The combination of glycosphingolipid synthase and a glycosphingolipid is preferably the combination of ganglioside synthase and a ganglioside, and more preferably, the combination of GM3 synthase and GM3. Combinations of other ganglioside synthases and gangliosides are shown in FIG. 1.

The screening method includes a method using an enzyme, as GM3 synthase used in the screening method described above, which is expressed in primary culture cells obtained from adipocytes, hepatocytes, vascular endothelial cells, vascular smooth muscle cells, skeletal muscle cells, epithelial cells, neurocytes, fibroblasts, monocytes, macrophages, etc. as well as in various cell lines (including, but not limited to, mouse 3T3-L1 in adipocytes; human HepG2 in hepatocytes; in endothelial cells, immortalized endothelial cell lines having an acetylated LDL uptake activity; RAW264.7 in macrophages; etc.), and a method using an enzyme produced by genetic engineering techniques, chemical synthesis, or the like are included. A preferred example is the enzyme derived from the nucleotide sequence described in SEQ ID NO: 1 or 3. The prepared GM3 synthase in this case may be in an isolated state or may not be in an isolated state. For instance, the above cells bearing the GM3 synthase may be used, or the GM3 synthase may be purified from the above cells. Alternatively, the GM3 synthase may also be prepared, for example, by using various culture cells, e.g., *Escherichia coli*, yeast, inset cells, mammal cells, etc. as a host and introducing an appropriate expression vector into the host, by genetic engineering. For these known methods, reference can be made to the methods described in, e.g., Molecular Cloning 3rd Ed. (J. Sambrook, et al, Cold Spring Harbour Laboratory Press, 2001), Current Protocols in Molecular Biology, John Wiley & Sons 1987-1997, etc.

The screening method of the present invention may also include, before administration of a test substance to a non-human animal, the step of contacting the test substance in vitro with cells expressing a preferred level of glycosphingolipid synthase, e.g., primary culture cells obtained from adipocytes, hepatocytes, vascular endothelial cells, vascular smooth muscle cells, skeletal muscle cells, epithelial cells, neurocytes, fibroblasts, monocytes, macrophages, etc. and various cell lines (including, but not limited to, mouse 3T3-L1 in adipocytes; human HepG2 in hepatocytes; in endothelial cells, immortalized endothelial cell lines having an acetylated LDL uptake activity; RAW264.7 in macrophages; etc.) etc., or with transformants prepared by genetic engineering, and determining the amount of glycosphingolipid selectively produced in these cells. The preferred combination of glycosphingolipid synthase to be determined and a glycosphingolipid includes the combination of ganglioside synthase and a ganglioside, and more preferably, the combination of GM3 synthase and GM3. The preferred expression level herein is intended to mean a normal or greater expression level in the organ from which each cell is derived. The other combinations of ganglioside synthases and gangliosides can be found in FIG. 1. For the genetic engineering techniques for producing the transformants described above, known methods described in, e.g., Molecular Cloning 3rd Ed. (J. Sambrook, et al, Cold Spring Harbour Laboratory Press, 2001), Current Protocols in Molecular Biology, John Wiley & Sons 1987-1997, etc. may be used.

For purification and quantitative detection of gangliosides, known methods can be used. For example, the method of Macher, B. A. and Klock, J. C. (J. Biol. Chem. 255, 2092-2096, 1980) or the method of Ledeen et al. (J. Neurochem. 21, 829-839, 1973) can be referred to. It is also possible to employ quantitative detection using an antibody which specifically acts on various ganglio sides, e.g., GM3. In such a screening method, the reduction level in the GM3 production amount by a test substance is at least 10% or more, preferably 20% or more, more preferably 40% or more, even more preferably 60% or more, still more preferably 80% or more, still more preferably 90% or more and 100%, when compared with the control.

In the screening method described above, the combination may be selective combination of at least one ganglio side described in FIG. 1, specifically at least one ganglioside selected from the group consisting of GM3, GM2, GM1, GD1a and GT1a (a-series) as well as GD3, GD2, GD1b, GT1b and GQ1b (b-series), and each ganglioside synthase. In such a screening method, the reduction level in the ganglioside production amount by a test substance is at least 10% or more, preferably 20% or more, more preferably 40% or more, even more preferably 60% or more, still more preferably 80% or more, 90% or more and 100%, when compared with the control.

The screening method of the present invention may include contacting a test substance with cells expressing a suitable level of glycosphingolipid synthase, e.g., primary culture cells obtained from adipocytes, hepatocytes, vascular endothelial cells, vascular smooth muscle cells, skeletal muscle cell, epithelial cells, neurocytes, fibroblasts, monocytes, macrophages, etc. and various cell lines (including, but not limited to, mouse 3T3-L1 in adipocytes; human HepG2 in hepatocytes; in endothelial cells, immortalized endothelial cell lines having an acetylated LDL uptake activity; RAW264.7 in macrophages; etc.) etc., and determining the selective expression level of GM3 synthase in these cells. The method for determining the expression level of GM3 synthase includes a method through hybridization utilizing a sequence of GM3 synthase, for example, northern blotting, a method utilizing a probe immobilized on a carrier, a method using a gene chip, quantitative PCR, etc. In such a screening method, for example, the suppression level of the expression for GM3 synthase by a test substance is 10% or more, preferably 20% or more, more preferably 40% or more, even more preferably 60% or more, and still more preferably 80% or more, 90% or more and 100%.

The test substance in the screening method of the present invention includes a polynucleotide which specifically inhibits the expression of GM3 synthase. Examples of the form of such a polynucleotide which inhibits the expression of GM3 synthase are the aforesaid antisense nucleic acid, ribozyme, double-strand RNA, etc. These polynucleotides which inhibit the expression of GM3 synthase can be prepared by a publicly-known method. Moreover, these nucleic acids may be subjected to various chemical modifications.

The screening method of the present invention also includes a method which comprises using a transgenic animal-derived cell or recombinant cell, in which a reporter gene is connected to the downstream of a promoter of GM3 synthase; contacting a test substance with the cell; and measuring the expression level of the reporter gene in the cell. As the recombinant cell to be used in this method, various cells may be used, and preferably, primary culture cells obtained from adipocytes, hepatocytes, vascular endothelial cells, vascular smooth muscle cells, skeletal muscle cells, epithelial cells, neurocytes, fibroblasts, monocytes, macrophages, etc., and various established cell lines (including, but not limited to, mouse 3T3-L1 in adipocytes; human HepG2 in hepatocytes; in endothelial cells, immortalized endothelial cell lines having an acetylated LDL uptake activity; RAW264.7 in macrophages; etc.), and the like. The gene sequence at the 5' upstream of GM3 synthase gene is described in Kim J-W, et al., Gene 273, 163-171, 2001, and the promoter is described in Kim S—W., et al., Biochim. Biophys. Acta 1578, 84-89, 2002; Choi H-J., et al., Biochem. Biophys. Res. Commun. 313, 142-147, 2004. Specifically, putative binding sites of transcription factors such as AP4, MZF1, SP1, ATF/CREB, NFY, IK2 and LYF1 have been found, and CREB has been additionally found which functions as a PMA-inducible promoter. Preferred examples of proteins encoded by the reporter gene to be used include various known proteins such as firefly luciferase, *Renilla* luciferase, green fluorescent protein (GFP), β-galactosidase, alkaline phosphatase, etc. These reporter proteins can be detected using a known detection method or kit. In such a screening method, for example, the suppression level of reporter protein expression upon stimulation by a test substance is 10% or more, preferably 20% or more, more preferably 40% or more, 60% or more, and even more preferably 80% or more, 90% or more and 100%.

2. Pharmaceutical Composition of the Invention

The present invention provides a pharmaceutical composition useful for treating and/or preventing hyperlipidemia, comprising the substance having the blood lipid level lowering activity.

The pharmaceutical composition of the present invention has the blood lipid level lowering activity, and preferably, can be used for the treatment or prevention of hyperlipidemia. Alternatively, the pharmaceutical composition of the present invention can be used for the treatment or prevention of diseases that can be treated by the blood lipid level lowering activity, for example, at least one disease selected from arteriosclerosis, atherosclerosis, peripheral vascular disease, hyper LDLemia, hypo HDLemia, hypercholesteremia, hypertriglyceridemia, familial hypercholesteremia, cardiovascular disturbance, angina pectoris, ischemia, cardiac ischemia, thrombosis, myocardial infarction, reperfusion damage, angioplasty restenosis and hypertension, and preferably, arteriosclerosis, hyper LDLemia, hypo HDLemia, hypercholesteremia, hypertriglyceridemia and familial hypercholesteremia. However, the present pharmaceutical composition reduces an abnormal blood lipid level in the subject down to nearly normal level.

The pharmaceutical composition of the present invention may contain a substance that specifically inhibits the functions of ganglioside. Preferably, the ganglioside may be GM3, and the substance that specifically inhibits the functions of ganglioside may be an anti-GM3 antibody. The pharmaceutical composition of the present invention may further contain a substance that selectively inhibits the functions of ganglioside. The substance includes, for example, a substance, e.g., an antibody, which can selectively inhibit, with GM3, a particular function among various functions, including the function of regulating the functions of various growth factor receptors on cell membranes, transport proteins, adhesive molecule receptors or functional proteins, raw material supply functions to various other gangliosides.

The pharmaceutical composition of the present invention may contain a substance that selectively inhibits ganglioside production. Such a substance may include a ganglioside synthase inhibitor, an expression inhibitor of this enzyme, etc., which is obtained by the screening method of the present invention described above.

Where the pharmaceutical composition of the present invention is used, the composition may be administered, for example, orally, intravenously, through the oral mucosa, rectally, vaginally, transdermally, intranasally, by inhalation, etc., and preferably, administered orally. The active component of the pharmaceutical composition of the present invention may be formulated solely or in combination. It is also possible to blend a pharmaceutically acceptable carrier or formulation additive therein to provide a formulation. In this case, the active component of the present invention can be contained in the formulation, for example, in an amount of 0.1 to 99.9 wt %.

The pharmaceutically acceptable carrier or additive, including, for example, an excipient, a disintegrant, a disintegrating aid, a binder, a lubricant, a coating agent, a dye, a diluent, a dissolving agent, a dissolving aid, a tonicity agent, a pH adjuster, a stabilizer, etc. can be used.

Examples of formulations suitable for oral administration include a powdered drug, a tablet, a capsule, a fine grain agent, a granular agent, a liquid drug, syrup, and the like. In the case of oral administration, various excipients such as microcrystalline cellulose, sodium citrate, calcium carbonate, dipotassium phosphate and glycine can be used in combination with: starch, preferably starch of corn, potato or tapioca; various disintegrants such as alginic acid and some of silicates; and a granulating binder such as polyvinyl pyrrolidone, sucrose, gelatin and gum arabic. Further, in many cases, lubricants such as magnesium stearate, sodium lauryl sulfate and talc are very effective for tablet formation. Such solid composition may be used with a gelatin capsule filled therein. In this regard, examples of preferred substances include lactose or milk sugar as well as a high-molecular-weight polyethylene glycol. When an aqueous suspension and/or elixir is desired for oral administration, active components are used in combination with a sweetener or a flavor and a colorant or a dye, and optionally in combination with an emulsifier and/or a suspending agent, and it can be used together with water, ethanol, propylene glycol, glycerin, etc., a diluent containing a combination thereof, etc.

Examples of the formulation suitable for parenteral administration include an injectable agent and a suppository. In the case of parenteral administration, a solution in which the active ingredient of the present invention is dissolved in sesame oil or peanut oil, or a solution in which the active component of the present invention is dissolved in an aqueous solution of propylene glycol can be used. An aqueous solution optionally may be buffered suitably (preferably pH 8 or higher), and a liquid diluent is firstly required to become isotonic. Such an aqueous solution is suitable for intravenous injection, and an oily solution is suitable for intraarticular injection, intramuscular injection and subcutaneous injection. Preparation of all of these solutions under aseptic conditions can be easily accomplished by the standard formulation technology well-known in the art. Moreover, the active ingredient of the present invention can be administered topically on the skin or the like. In this case, it is desirably administered topically in the form of cream, jelly, paste or ointment according to the standard pharmaceutical practice.

The dose of the pharmaceutical composition of the present invention is not particularly limited, and an appropriate dose can be chosen depending on various conditions such as the type of disease, age and symptoms of the patient, administration route, therapeutic goal, presence or absence of concurrent drugs, etc. The dose of the pharmaceutical composition of the present invention is, for example, 1 to 5,000 mg, and preferably 10 to 1,000 mg per day for an adult (e.g., body weight: 60 kg). The composition of such daily dosage may be administered daily in 2 to 4 divided doses.

3. Method for Treatment of the Invention

In the method for treatment according to the present invention, the substance having the blood lipid level lowering activity is the substance capable of reducing a blood lipid level down to nearly normal level, as described above. Examples of the substance include a substance which suppresses the production level of glycosphingolipid expressed in primary culture cells obtained from adipocytes, hepatocytes, vascular endothelial cells, vascular smooth muscle cells, skeletal muscle cells, epithelial cells, neurocytes, fibroblasts, monocytes, macrophages, etc., and various cell lines (including, but not limited to, mouse 3T3-L1 in adipocytes; human HepG2 in hepatocytes; in endothelial cells, immortalized endothelial cell lines having an acetylated LDL uptake activity; RAW264.7 in macrophages; etc.), a substance which suppresses the production level of ganglioside expressed in these cells, a substance which suppresses the production level of GM3 expressed in these cells, GM3 synthase inhibitors, a substance which suppresses the expression of GM3 synthase, etc. The pharmaceutical composition comprising these substances having the blood lipid level lowering activity is prepared as described above, and can be administered to the subject in need thereof. In this case, dose, frequency of dosing, etc. may be appropriately controlled by a physician with considering age, medical history, drugs currently used, etc. of the subject. Thus, the prevention or treatment of hyperlipidemia, etc. or control of a lipid level in blood in the subject can be achieved.

EXAMPLES

Hereinafter, the present invention is described more specifically by referring to EXAMPLES. These descriptions are presented only for illustrative and should not be construed as limiting the present invention to these EXAMPLES.

1. Generating SAT-I KO Mice

The schematic diagram of a targeting vector used for generation of the SAT-I KO mice and confirmation of genetic defect in the KO mice are shown in FIG. 2A and FIG. 2B, respectively. In FIG. 2A, the targeting vector is shown at the top, a wild-type gene at the second row, and a variant gene at the third row. Furthermore, FIG. 2B shows determination of the SAT-I genotype by PCR. For identification of the wild-type SAT I genomic allele (exon 2), 5'-GGAATCCATC-CCTTTTCTCACAGAG-3 (SEQ ID NO: 5) and 5'-TGAACTCACTTGGCATTGCTGG-3' (SEQ ID NO: 6) were used as primers. To confirm the SAT-I knockout, the neomycin-resistant gene inserted in the genome and the primers of 5'-GGAATCCATCCCTTTTCTCACAGAG-3' (SEQ ID NO: 7) and 5'-TGAACTCACTTGGCATTGCTGG-3' (SEQ ID NO: 8) were used. FIG. 2C shows the results of TLC analysis of brain ganglioside. In the wild-type mice (+/+) and the heterozygous mice (+/−), GM1, GD1a, GD1b, GT1b, etc. were expressed, while in the knockout mice (−/−), these all disappeared, and GM1b and GD1a were expressed in a compensatory manner (see FIG. 1).

2. Generating SAT-I/apoE Double Knockout Mice

ApoE is one of the major apolipoproteins and a constituent of lipoproteins including chylomicrons (CM), very low density lipoproteins (VLDL), intermediate density lipoproteins (IDL), low density lipoproteins (LDL), etc., and involved in transport of cholesterol or triglycerides. ApoE is produced mainly in the liver and functions as a ligand for the lipoprotein when the lipoprotein binds to LDL receptors, VLDL receptors, LDL-receptor related protein (LRP) receptors, etc. to transport extracellular lipids into the cells.

Figure 2:
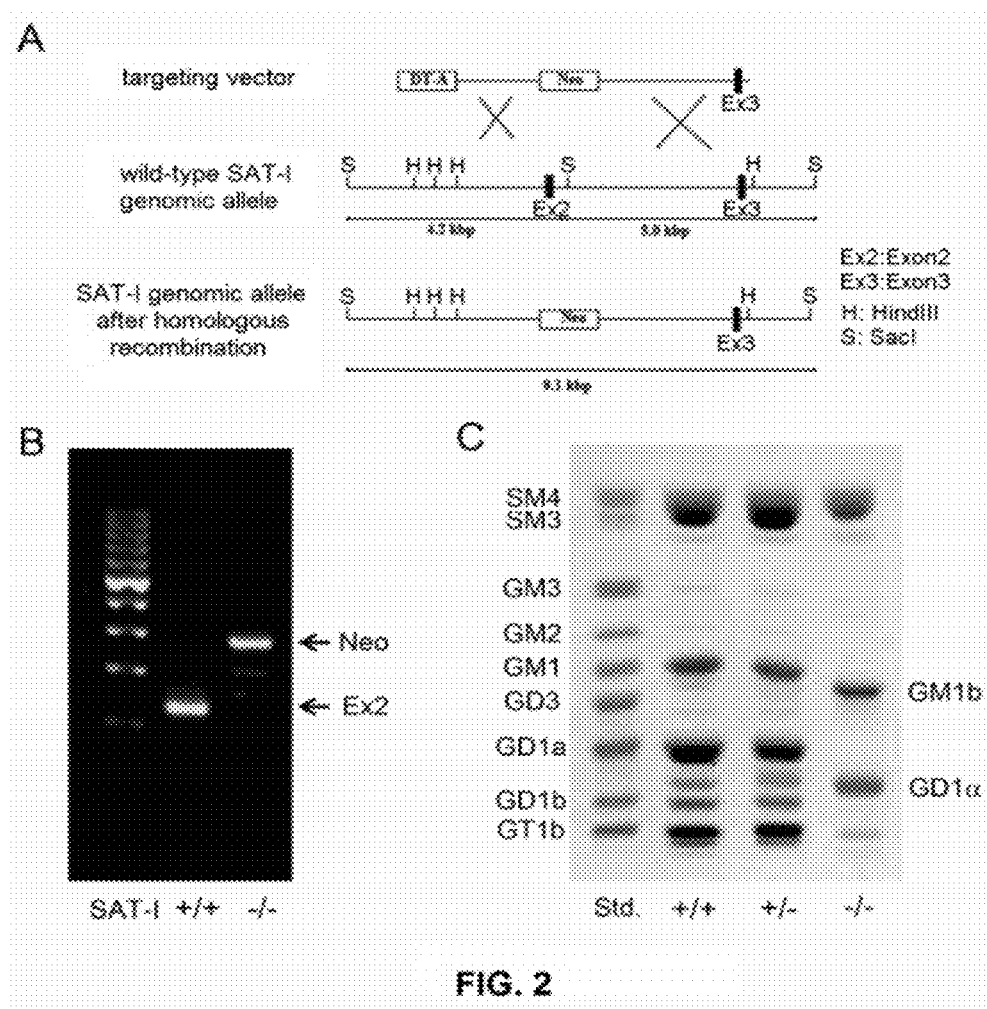
FIG. 2 shows the method for preparing GM3 synthase gene knockout mice (SAT-I KO).
Figure 3:
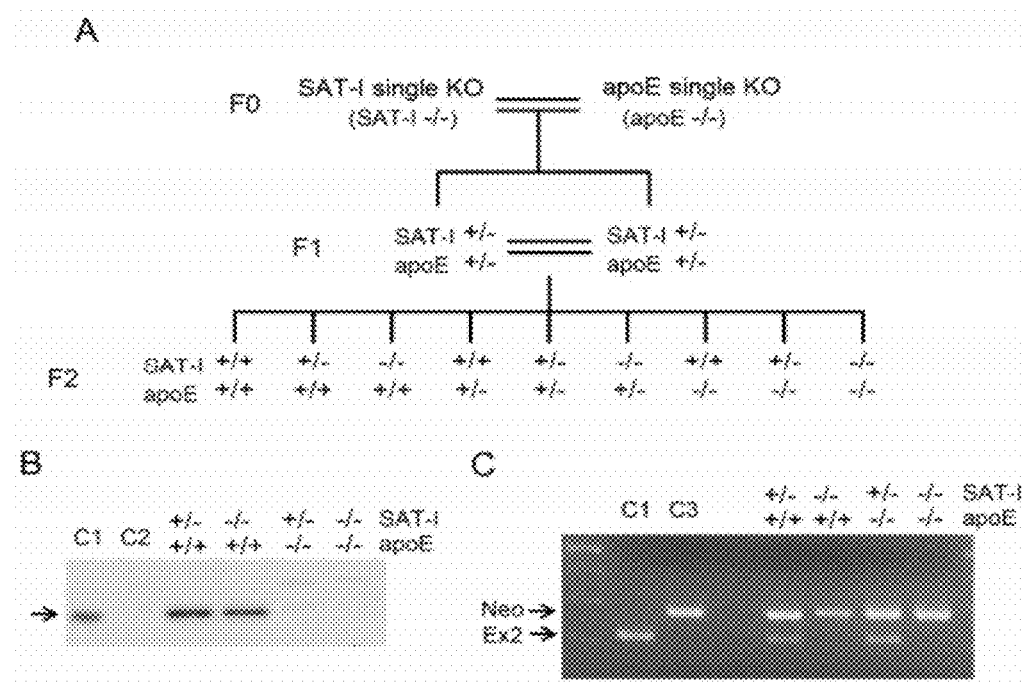
FIG. 3 shows the preparation of SAT-I/apoE double knockout (DKO) mice and confirmation of the genes.

SAT-I/apoE double knockout mice were generated by breeding SAT-I knockout mice generated independently (Yoshikawa M, Go S, Takasaki K, Kakazu Y, Ohashi M, Nagafuku M, Kabayama K, Sekimoto J, Suzuki S, Takaiwa K, et al. (2009) Proc. Natl. Acad. Sci. USA 106, 9483-9488. Epub 2009 May 9422) (FIG. 2) with spontaneously apoE deficient-hyperlipidemic model mice (hereafter, apoE deficient mice) established by Matsushima et al. (Matsushima Y., Hayashi S., & Tachibana M. (1999) Mamm. Genome 10, 352-357; Matsushima Y., Sakurai T., Ohoka A., Ohnuki T., Tada N., Asoh Y., & Tachibana M. (2001) J. Atheroscler. Thromb. 8, 71-79) (FIG. 3). More specifically, the animal was prepared as follows.

The mice with either SAT-I or apoE deficient (F0 generation) were bred with each other to produce the F1 generation mice heterozygous for both genes. Subsequently, the F1 generation mice were bred with each other to produce SAT-I/apoE double knockout mice in the F2 generation (FIG. 3A).

In the resulting SAT-I/apoE double knockout mice, it was confirmed by western blotting if apoE protein was expressed. In FIG. 3B, the band at the position marked with the arrow shows apoE protein, lane C1 designates normal mouse and lane C2 designates a control sample for the apoE single knockout mouse.

The expression of SAT-I gene was also confirmed by PCR. Specific procedures are the same as in FIG. 2B. In FIG. 3C, lane C3 designates the control sample for the SAT-I single knockout mouse. Ex2 marked with the arrow designates normal SAT-I gene exon 2, and Neo marked with the arrow designates the neomycin resistant gene.

Figure 4:
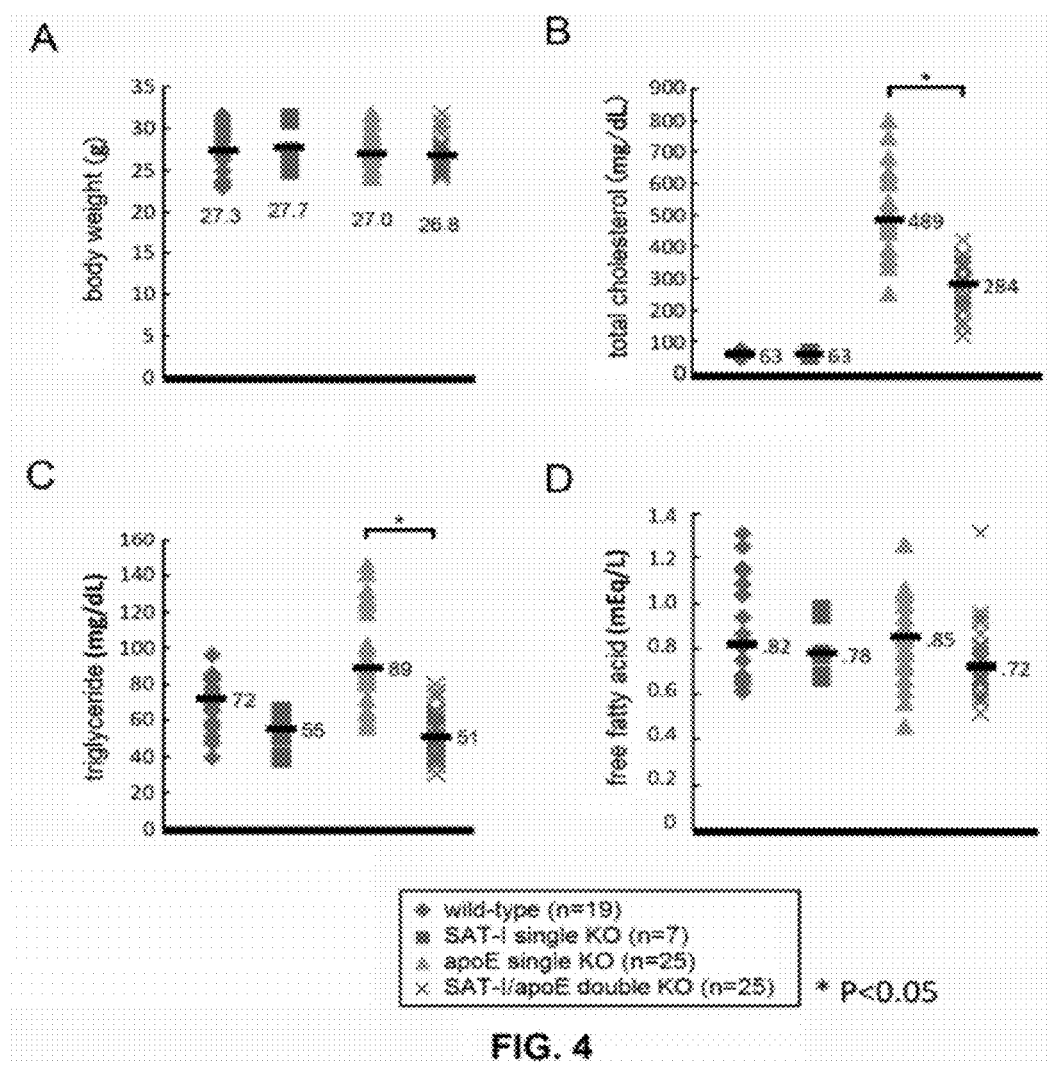
FIG. 4 shows the assay results of the body weight and blood lipid level of SAT-I/apoE double knockout mice in FIG. 3.

3. Assay for Body Weight and Blood Lipid Level in SAT-I/apoE Double Knockout Mice Wild-type, SAT-I single knockout, apoE single knockout and SAT-1/apoE double knockout mice (male mice at 16-18 weeks old, all fed with normal diet) were examined for the body weight and blood lipid level. Specifically, after the wild-type, SAT-I single knockout, apoE single knockout and SAT-I/apoE double knockout mice (male mice at 16-18 weeks old) were fasted for 16 hours, the body weight was measured and blood was then collected under heparin. Lipids were assayed in plasma. As a result of the analysis, there was no significant difference in the body weight among all strains of mice (FIG. 4A). The cholesterol level and TG level in plasma were 489 mg/dl and 89 mg/dl, respectively, for the apoE single knockout mice, as already reported, indicating markedly high levels when compared with those of wild-type mice (cholesterol level: 63 mg/dl, TG level: 72 mg/dl) (FIGS. 4A and C). On the other hand, the cholesterol and TG levels in plasma for the SAT-I/apoE double knockout mice were 284 mg/dl and 51 mg/dl, respectively, indicating remarkable reduction as compared with those of the apoE single knockout mice (FIGS. 4B and C). In particular, the TG level was normalized to the same level as in the wild-type. As such, it was revealed that abnormal cholesterol and TG levels in hyperlipidemic model mice were improved to normal levels by knocking out SAT-I. In addition, there was no significant change in free fatty acid level in blood among all strains of mice (FIG. 4D).

Figure 5:
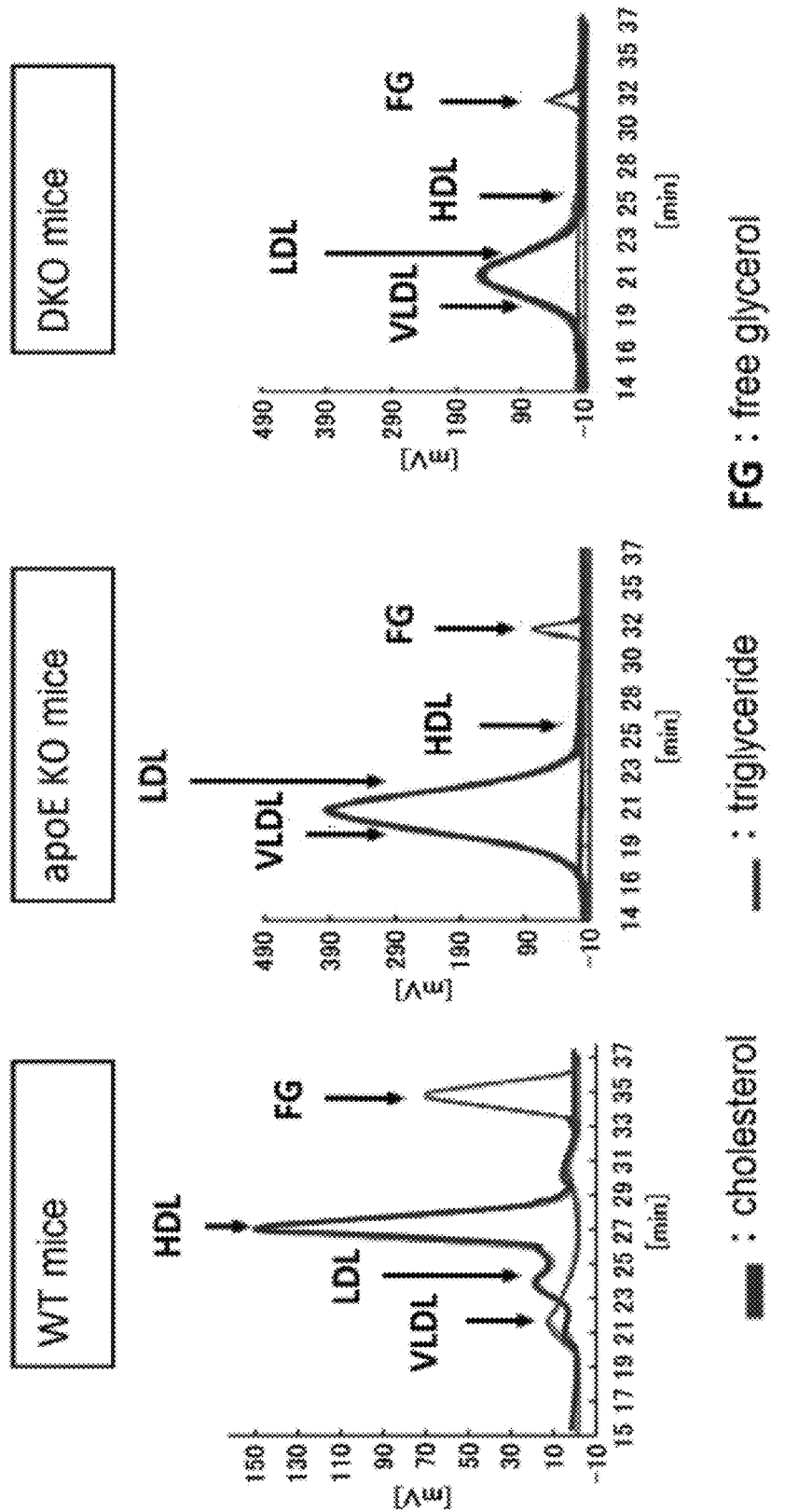
FIG. 5 shows the profiles of plasma lipoproteins from ApoE knockout mice and SAT-I/ApoE double knockout mice, which were fractionated with gel filtration high performance chromatography.

The lipoproteins were isolated from the sera of these mice and the profiles were compared. The serum lipoproteins isolated were fractionated by particle size using gel filtration high performance chromatography (which was performed by the method described in Usui, S. et al., J. Lipid Res. 43, 805-814, 2002), and the cholesterol and triglyceride in each fraction were quantified. The results are shown in the waveform graph (FIG. 5) and TABLE 1 below. In the SAT-I/apoE double knockout (DKO) mice, a decrease in plasma total cholesterol and triglyceride was shown, as compared to the apoE knockout (apoE KO) mice, and the decrease was found to be mainly due to a decrease in lipoproteins of CM, VLDL and LDL.

TABLE 1

Comparison of cholesterol and TG contents in serum lipoprotein fractions between apoE knockout mice and DKO mice

| Genotype | total*** | CM*** | VLDL*** | LDL** | HDL* |
|---|---|---|---|---|---|
| | Cholesterol (mg/dL) | | | | |
| apoE KO (n = 3) | 587 ± 0.75 | 8.00 ± 0.75 | 434 ± 50 | 131.8 ± 1.06 | 11.8 ± 2.04 |
| DKO (n = 3) | 259 ± 52.9 | 2.59 ± 0.76 | 168 ± 64 | 78.3 ± 8.05 | 10.0 ± 0.51 |
| % DKO/apoE KO | 44.1% | 32.4% | 38.7% | 59.4% | 84.7% |
| | TG (mg/dL) | | | | |
| apoE KO (n = 3) | 59.04 | 19.28 | 31.05 | 6.72 | 1.88 |
| DKO (n = 3) | 34.65 | 12.13 | 15.98 | 5.27 | 1.28 |
| % DKO/apoE KO | 58.1% | 62.9% | 51.5% | 78.2% | 68.0% |

Significance of the DKO value as compared to each value of apoE KO is indicated by
*p < 0.05,
**p < 0.01 and
***p < 0.00.

Figure 6:
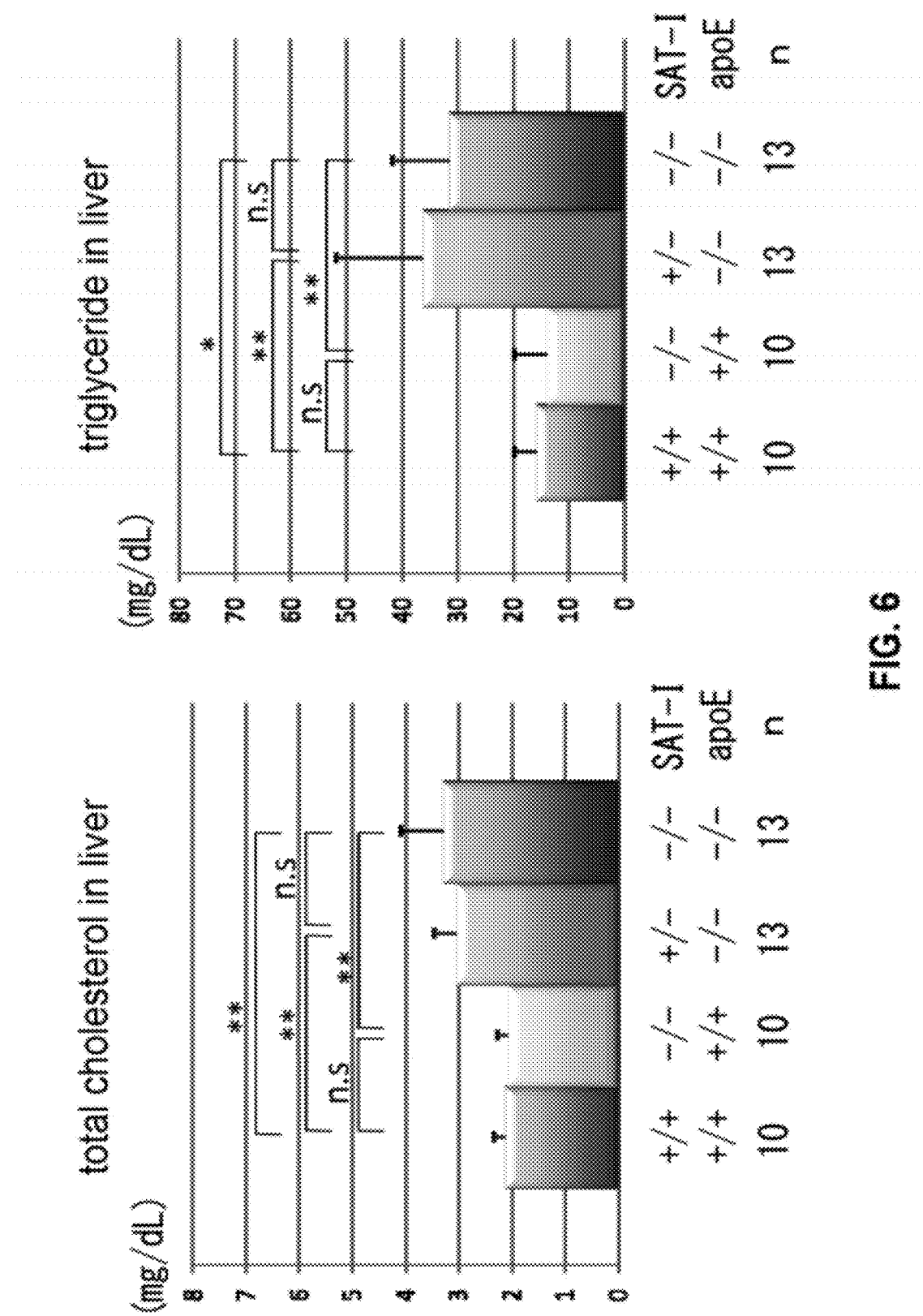
FIG. 6 shows the change in the lipid composition in the livers of ApoE knockout mice and SAT-I/ApoE double knockout mice.

Next, the lipid level in the liver was examined. The liver was dissected from each mouse and PBS was added thereto. The liver was minced with scissors and then homogenized with a Polytron Homogenizer 3100. After the homogenized suspension was transferred to a centrifuging tube, chloroform/methanol (1:2, v/v) was added to the homogenate and incubated at 40° C. to extract the lipids. Subsequently, the extract was centrifuged and the supernatant was recovered. After chloroform/methanol (1:2, v/v) was added to the centrifuge precipitate, incubation was performed in a similar manner followed by centrifugation. The supernatant was recovered and hexane was further added to the centrifuge precipitate followed by incubation at 40° C. After centrifugation, the supernatant was recovered. All of the supernatants were pooled to give the total lipid extract. The extract was then evaporated to dryness under nitrogen. To further purify the lipid components from the total lipid extract, the extract was evaporated to dryness under nitrogen and then $CHCl_3$ was added, followed by ultrasonication. Purified water was added to mix them and the mixture was centrifuged. After centrifugation, the mixture was separated into the upper layer (aqueous layer), intermediate layer (protein layer) and lower layer (chloroform layer). Only the lower layer was taken out of the three layers and evaporated to dryness under nitrogen. The total lipid extract purified was dissolved in an aqueous solution containing 2% Triton X-100 and 2% sodium cholate. The cholesterol level and the triglyceride level were then assayed using a Cholesterol E-Test Wako (Wako Pure Chemical Industries, Ltd) and a TG-EN Kainos (Kainos Laboratories), respectively (FIG. 6). A significant increase both in cholesterol and triglyceride levels was observed in the apoE knockout mice, as compared to the wild-type mice (FIG. 6; *: $p<0.05$, : $p<0.01$, *: $p<0.001$), whereas in the SAT-I/apoE double knockout mice, no significant difference was observed when compared with the apoE knockout mice (FIG. 6; designated by n.s.).

Next, the expression of glycosphingolipids was analyzed in the plasma and liver of apoE knockout mice, SAT-I/apoE double knockout mice and wild-type mice. The method for analysis of glycosphingolipids is described below. To 1 ml of mouse plasma was added 8 mL of chloroform/methanol (1:1, v/v). The resulting mixture was ultrasonicated in a water bath with an ultrasonic generator, incubated at 40° C. and centrifuged to recover the supernatant. To the centrifuge precipitate was again added 8 mL of chloroform/methanol (1:2, v/v). The mixture was ultrasonicated, incubated at 40° C. and centrifuged to recover the supernatant. The supernatant was pooled with the supernatant from the previous centrifugation. The pooled supernatant was then evaporated to dryness under nitrogen to give the total lipid extract. To separate the total lipid extract into neutral lipids and acidic lipids, a DEAE column obtained by packing a glass filter-equipped column (($\phi$10 mm) with DEAE-Sephadex A-25 (GE Healthcare) was used. The total lipid extract was dissolved in chloroform/methanol/purified water (30:60:8, v/v). The solution was charged onto the DEAE column. Then, chloroform/methanol/purified water (30:60:8, v/v) was passed through the column to elute the neutral lipids. Subsequently, chloroform/methanol/1N sodium acetate aqueous solution (30:60:8, v/v) was passed through the column to elute the acidic lipids. The respective eluates were evaporated to dryness under nitrogen. Next, alkaline methanolysis was performed to degrade the glycerol skeleton fats contained in each lipid fraction. After addition of 0.1M sodium hydroxide/methanol solution, the mixture was ultrasonicated and incubated at 40° C. Thereafter, 1N hydrogen chloride/methanol solution was added to neutralize the solution. Subsequently, 50 mM sodium chloride aqueous solution was added thereto. The resulting mixture was passed through a Sep-Pak C18 Cartridge (Waters Associates, Inc.), and then purified water was passed for desalting. The first round of lipids was eluted with methanol. Furthermore, the second round of elution was performed using chloroform/methanol (2:1, v/v) for the neutral lipid fraction and using chloroform/methanol (1:2, v/v) for the acidic lipid fraction. After elution, the eluate was evaporated to dryness and the residue was dissolved in a small amount of chloroform/methanol. The solution was spotted onto a silica gel plate for TLC (Merck & Co., Inc.). Separation of the lipids was performed as follows. A first development was carried out with chloroform alone. After drying the plate, a second development for the acidic lipid fraction was carried out with chloroform/methanol/0.2% calcium chloride aqueous solution (55:45:10, v/v). For the neutral lipid fraction, a second development was performed with chloroform/methanol/purified water (60:40:10, v/v). Following the development, orcinol-sulfuric reagent (coloring reagent for compounds with a sugar chain structure) was sprayed and heated to approximately 120° C. to produce a color. The bands detected were quantified with a network scanner and an image processing software (Image J).

Figure 7:
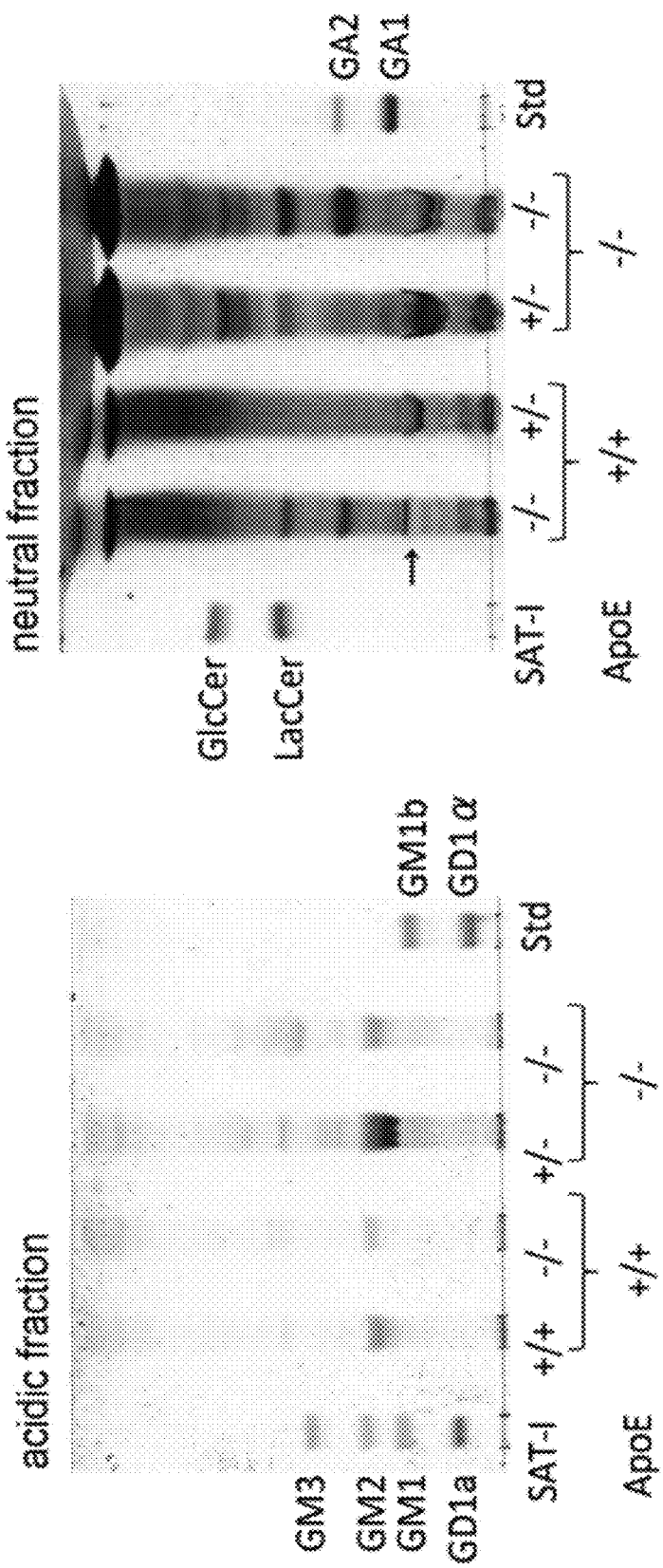
FIG. 7 shows the analysis results of plasma glycosphingolipids from SAT-I knockout mice, ApoE knockout mice and SAT-I/ApoE double knockout mice.

As shown in FIG. 7, the major glycosphingolipid in plasma was GM2 in the wild-type mice, and GM2, GlcCer and LacCer were increased in the neutral fraction of the apoE knockout mice. On the other hand, GM2 was detected also in the acidic fraction of SAT-I knockout mice, even though small, as compared to the wild-type mice. Also in the neutral fraction of SAT-I knockout mice, compensatory increase of LacCer and GA2 was observed. The same expression patterns as in the SAT-I knockout mice were found also in the acidic fraction and neutral fraction of SAT-I/apoE double knockout mice.

Figure 8:
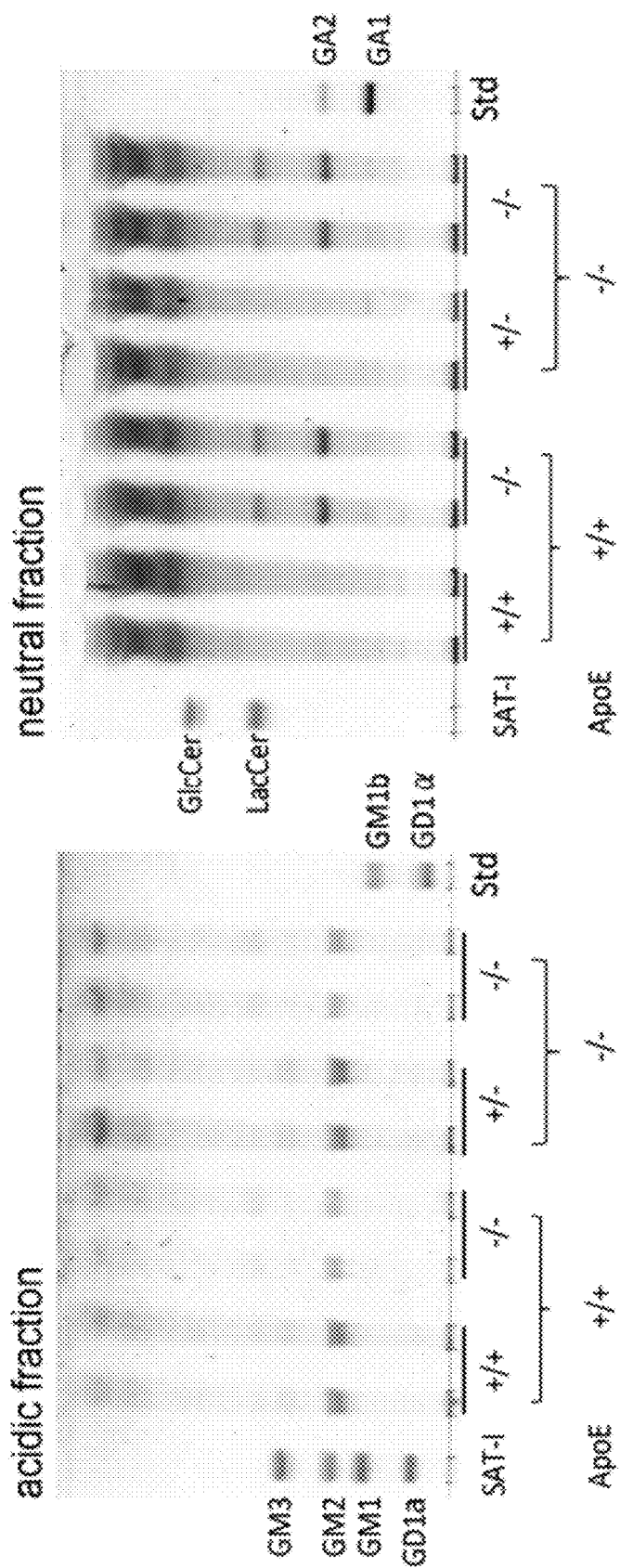
FIG. 8 shows the analysis results of glycosphingolipids in the livers of SAT-I knockout mice, ApoE knockout mice and SAT-I/ApoE double knockout mice.

Next, the analysis results of glycosphingolipids in the liver are shown in FIG. 8. It was confirmed that the major glycosphingolipid in the liver was GM2 in the wild-type mice. On the other hand, GM2 was detected also in the acidic fraction of SAT-I knockout mice, even though small, as compared to the wild-type mice. Also in the neutral fraction of SAT-I knockout mice, compensatory increase of LacCer and GA2 was observed. Further in the apoE knockout mice and the SAT-I/apoE double knockout mice, the same expression patterns as in the wild-type and the SAT-I knockout mice were found, respectively; there was no difference in expression level between the two groups.

Figure 9:
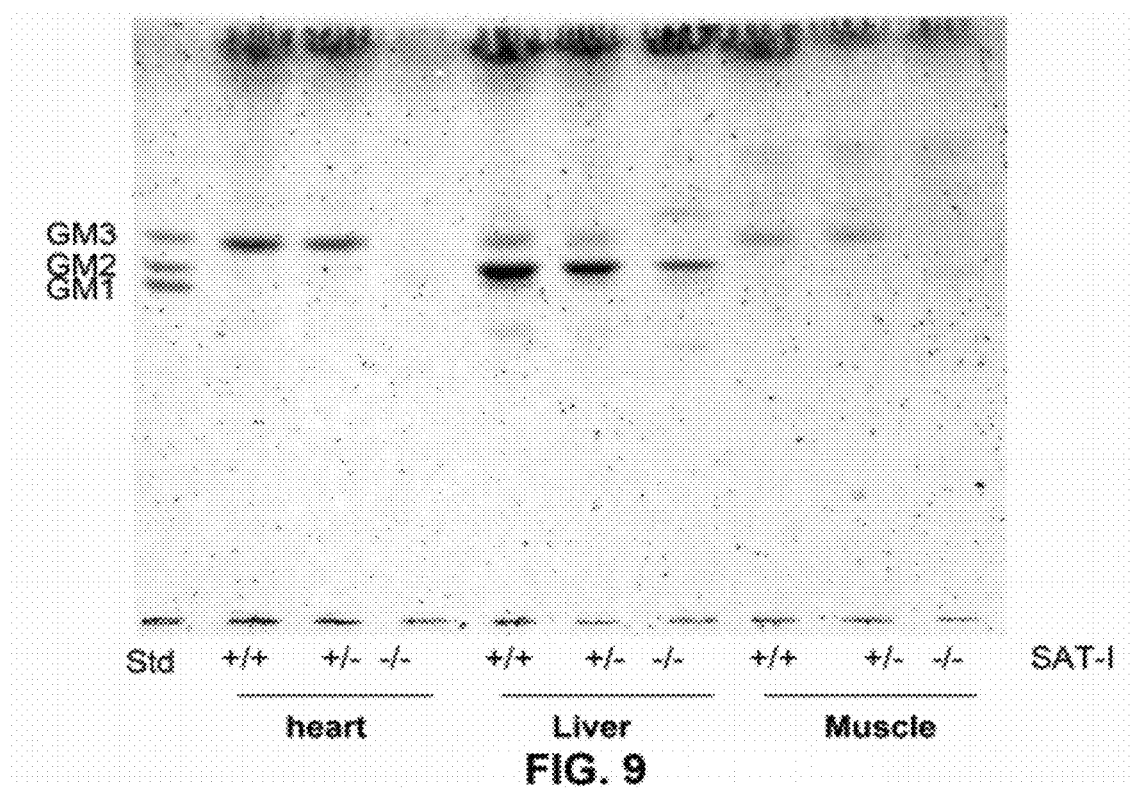
FIG. 9 shows the assay results of the ganglioside composition in the hearts, livers and muscles of SAT-I knockout mice and wild-type mice.

The analysis results of gangliosides in the heart, liver and muscle of the SAT-I knockout mice and wild-type mice are given in FIG. 9. The expression of GM2 was observed only in the liver. In the SAT-I knockout mice employed in this study, exon 2 of the SAT-I gene and its flanking regions are replaced with the neomycin-resistant gene (FIG. 2). As a result of the gene analysis of SAT-I gene in the liver, the possibility was suggested that SAT-I variants, which do not require exon 2, might be specifically expressed in the liver. It was further confirmed, in the other SAT-I knockout mouse lacking exon 6 which encodes the enzymatically catalytic domain in SAT-1, that GM2 was not expressed in the liver, which also indicates that SAT-I is the only one enzyme for the synthesis of GM3. From the foregoing, GM2 observed in the plasma and liver of SAT-I knockout mice is considered to be derived from the liver.

The foregoing results are summarized as follows.

1) The plasma total cholesterol and triglyceride levels were reduced in the SAT-I/apoE double knockout mice down to about a half the level of the apoE knockout mice. The decrease was due to the CM, VLDL and LDL fractions.

2) With regard to the glycosphingolipid composition in the plasma and liver, the ganglioside level was decreased by the SAT-I gene defect, and the neutral glycosphingolipids including GlcCer, LacCer, GA2, GA1, etc. were increased in a compensatory manner.

3) In the liver where endogenous cholesterol and triglycerides are synthesized and VLDL that transports them is synthesized, it was examined if there is a difference in the cholesterol level and the triglyceride level. As a result, no significant difference was seen between the SAT-I/apoE double knockout mice and the apoE knockout mice.

Based on 1) and 2), the possibility was suggested that the synthesis, metabolism and excretion of cholesterol and triglycerides as well as the synthesis, release and tissue-uptaking of VLDL, etc. might be affected in the plasma or liver by the decreased gangliosides or the increased glycosphingolipids in a compensatory manner. Based on 3), even if there was no difference between cholesterol and triglyceride levels in the liver, differences were observed in their synthesis, metabolism, excretion, etc. Thus, these results in total suggested that the increase of plasma total cholesterol and plasma triglycerides is prevented.

To further confirm the results, the SAT-I knockout mice were fed with high cholesterol diet, and the cholesterol and triglyceride levels in the sera were compared with those of the wild-type mice.

Figure 10:
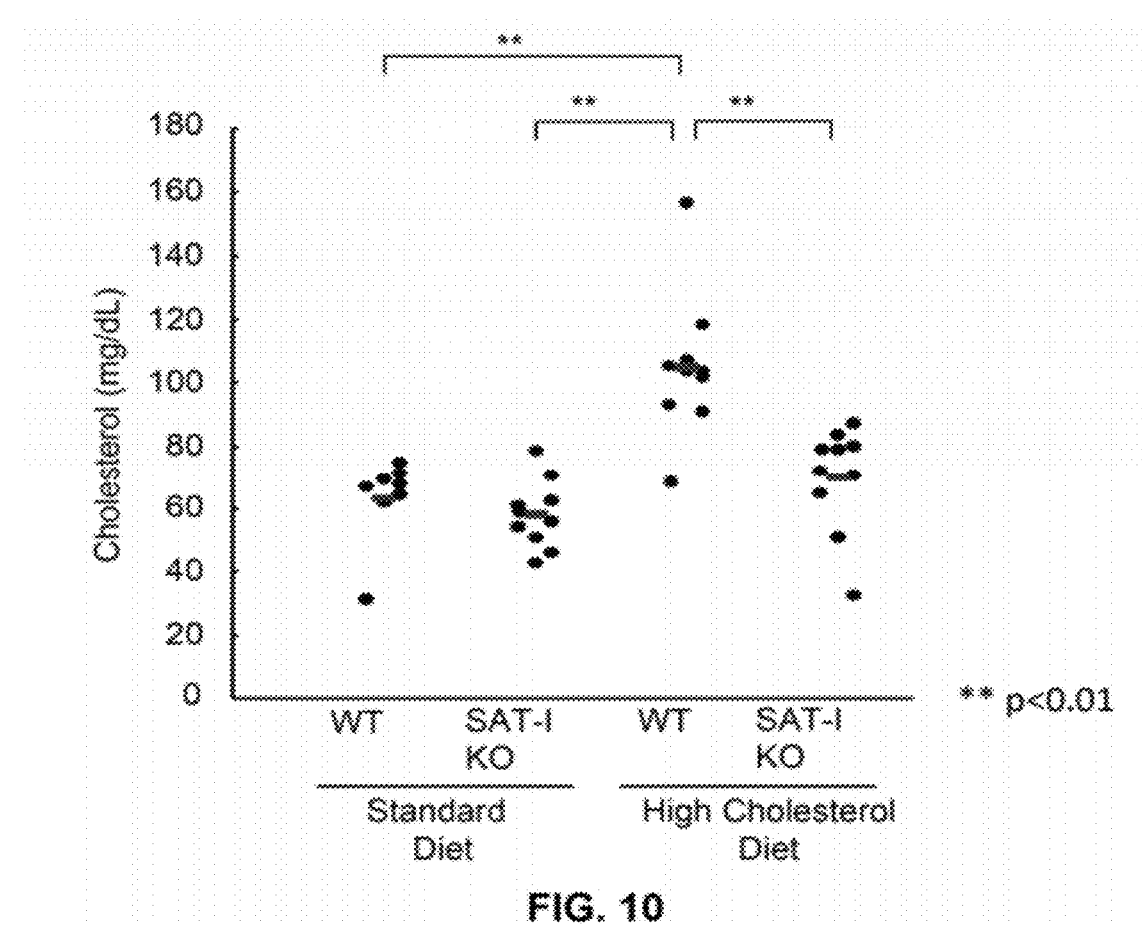
FIG. 10 shows the assay results of plasma lipids in SAT-I knockout mice fed with high cholesterol diet.

After the wild-type mice and the SAT-I KO mice were fed with high cholesterol diet for 10 weeks, the sera were collected therefrom. The total cholesterol and free fatty acids were quantitatively determined using a kit available from Wako Pure Chemicals. Statistical analysis of the total cholesterol was performed using Scheffe's F test, and statistical analysis of free fatty acids was according the Tukey-Kramer method. The results indicate that the increase in serum cholesterol level observed when the wild-type mice were fed with high cholesterol diet was not observed at al when the SAT-I KO mice were fed with high cholesterol diet (FIG. 10).

The foregoing results reveal, for the first time, that hyperlipidemia could be treated by suppressing the biosynthesis of gangliosides through regulation of the SAT-I gene expression (not the regulation of all GSLs expressions).

INDUSTRIAL APPLICABILITY

The present invention is a novel and revolutionary invention, in which blood lipid level can be reduced to nearly normal level through the selective regulation of ganglioside GM3. Based on the present invention, it is expected to develop a novel method for preventing/treating hyperlipidemia and furthermore, a novel method for preventing/treating atherosclerosis, hyper LDLemia, hypo HDLemia, hypercholesteremia, hypertriglyceridemia and familial hypercholesteremia.

The invention claimed is:

1. A method for screening a GM3 synthase specific inhibitor having a blood lipid level lowering activity that specifically inhibits GM3 synthase expression, which comprises:
   contacting a test substance with a cell selected from the group consisting of an adipocyte and a hepatocyte, wherein the cell expresses GM3 synthase;
   selecting a test substance that specifically decreases the expression level of GM3 synthase as compared to a control;
   administering the selected test substance to a non-human apoE-deficient animal; and
   determining a Chylomicron (CM) level, a Very Low Density Lipoprotein (VLDL) level or a Low Density Lipoprotein (LDL) level in blood in the non-human apoE-deficient animal and selecting a test substance having a blood lipid level lowering activity that specifically inhibits GM3 synthase expression and reduces the CM, VLDL or LCL level in blood by 10% or more as compared to a control.

2. The screening method according to claim 1, which further comprises selecting a test substance that reduces a blood cholesterol level and/or a blood triglyceride level.

3. The method according to claim 1, wherein the non-human animal has a higher blood lipid level than normal level.

4. The method according to claim 1, wherein the non-human animal is a mouse.

* * * * *